(12) United States Patent
Gao et al.

(10) Patent No.: US 10,596,173 B2
(45) Date of Patent: Mar. 24, 2020

(54) COMBINATION THERAPY OF AN HBV CAPSID ASSEMBLY INHIBITOR AND AN INTERFERON

(71) Applicant: Hoffmann-La Roche Inc., Little Falls, NJ (US)

(72) Inventors: Lu Gao, Shanghai (CN); Isabel Najera, Basel (CH); Hong Shen, Shanghai (CN); Fang Shen, Shanghai (CN); Liping Shi, Shanghai (CN); Steffen Wildum, Basel (CH); Guang Yang, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/970,128

(22) Filed: May 3, 2018

(65) Prior Publication Data
US 2018/0250301 A1    Sep. 6, 2018

Related U.S. Application Data

(63) Continuation of application No. PCT/EP2016/076195, filed on Oct. 31, 2016.

(30) Foreign Application Priority Data

Nov. 3, 2015   (WO) ................ PCT/CN2015/093688

(51) Int. Cl.
| | | |
|---|---|---|
| *A61K 31/506* | (2006.01) | |
| *A61K 38/21* | (2006.01) | |
| *A61P 31/12* | (2006.01) | |
| *A61K 31/5377* | (2006.01) | |

(52) U.S. Cl.
CPC ........ *A61K 31/506* (2013.01); *A61K 31/5377* (2013.01); *A61K 38/212* (2013.01); *A61P 31/12* (2018.01); *A61K 2300/00* (2013.01)

(58) Field of Classification Search
CPC . C07D 471/04; A61K 31/4985; A61K 31/506
See application file for complete search history.

(56) References Cited

U.S. PATENT DOCUMENTS

| | | | |
|---|---|---|---|
| 9,233,978 B2 * | 1/2016 | Guo .................... | A61K 31/4985 |
| 10,081,627 B2 * | 9/2018 | Guo .................... | A61K 31/4985 |
| 2015/0252057 A1 * | 9/2015 | Guo .................... | A61K 31/4985 |
| | | | 514/230.5 |

FOREIGN PATENT DOCUMENTS

| | | |
|---|---|---|
| CN | 103664925 A | 9/2013 |
| EP | 0236 987 A2 | 9/1987 |
| EP | 0510 356 A1 | 10/1992 |
| EP | 0593 868 A1 | 4/1994 |
| EP | 0809996 A2 | 5/1997 |
| WO | 95/13090 | 5/1995 |
| WO | 01/45712 A1 | 6/2001 |
| WO | 2001/45712 A1 | 6/2001 |
| WO | 2008/154817 A1 | 12/2008 |
| WO | 2008/154818 A1 | 12/2008 |
| WO | 2008/154819 A1 | 12/2008 |
| WO | 2008/154820 A1 | 12/2008 |
| WO | 2014/037480 A1 | 3/2014 |
| WO | 2014/184328 A1 | 11/2014 |
| WO | 2015/074546 A1 | 5/2015 |
| WO | 2015/120178 A1 | 8/2015 |
| WO | 2015/132276 A1 | 9/2015 |

OTHER PUBLICATIONS

Brook et al. Gut, 1989, 30(8): 1116-22 (abstract only).*
Hui et al. Expert Rev Anti Infect Ther, 2005, 3(4): 495-504 (abstractonly).*
Boni et al., "Characterization of hepatitis B virus (HBV)-specific T-cell dysfunction in chronic HBV infection" J Virol 81(8):4215-4225 (Apr. 2007).
Brezillon et al., "Antiviral activity of Bay 41-4109 on hepatitis B virus in humanized Alb-uPA/SCID mice" PLoSONE 6(12 Suppl 1-6):e25096 (Dec. 2011).
Buster et al., "Peginterferon alpha-2b is safe and effective in HBeAg-Positive chronic hepatitis B patients with advanced fibrosis" Hepatology 46:388-394 ( 2007).
Chou et al., "Theoretical Basis, Experimental Design, and Computerized Simulation of Synergism and Antagonism in Drug Combination Studies" Pharmacological Reviews 58(3):621-681 ( 2006).
Christen et al., "Inhibition of Alpha Interferon Signaling by Hepatitis B Virus" J. Virol. 81:159-165 ( 2007).
Craig et al., "Antiviral synergy between inhibitors of HIV proteinase and reverse transcriptase" Antiviral Chemistry & Chemotherapy 4:161-166 ( 1990).
Deres et al., "Inhibition of Hepatitis B Virus Replication by Drug-Induced Depletion of Nucleocapsids" Science 299(5608):893-897 (Feb. 7, 2003).
Fisicaro et al., "Antiviral intrahepatic T-cell responses can be restored by blocking programmed death-1 pathway in chronic hepatits B" Gastroenterology 138:682-693 ( 2010).
Guan et al., "Interferon-a response in chronic hepatitis B-transfected HepG2.2.15 cells is partially restored by lamivudine treatment" World J Gastroenterol 13(2):228-235 ( 2007).
ISR of PCT/EP2016/076195 (Date of mailing Jan. 19, 2017).

(Continued)

*Primary Examiner* — Rei Tsang Shiao

(74) *Attorney, Agent, or Firm* — Genentech, Inc.; Richard G. A. Bone

(57) ABSTRACT

The present invention is directed to compositions and methods for treating hepatitis B virus infection. In particular, the present invention is directed to a combination therapy comprising administration of an HBV capsid assembly inhibitor and an interferon for use in the treatment of hepatitis B virus infections.

25 Claims, 2 Drawing Sheets
Specification includes a Sequence Listing.

(56) References Cited

OTHER PUBLICATIONS

Janssen et al., "Pegylated interferon alfa-2b alone or in combination with lamivudine for HBeAg-positive chronic hepatitis B: a randomised trial" Lancet 365:123-129 (Jan. 8, 2005).

Kondo et al., "Hepatitis B surface antigen could contribute to the immunopathogenesis of hepatitis B virus infection" ISRN Gastroenterology (Article ID 935295), 2013.

Kondo et al., "Recovery of functional cytotoxic T lymphocytes during lamivudine therapy by acquiring muti-specificity" J Med Virol 74:425-433 ( 2004).

Lambert et al., "Posttranslational N-glycosylation of the hepatitis B virus large envelope protein" Virol J 4( Suppl 1-9):45 (May 2007).

Lau et al., "Peginterferon Alfa-2a, lamivudine, and the combination for HBeAg-positive chronic hepatitis B" New Engl J Med 352:2682-2695 ( 2005).

Marcellin et al., "Peginterferon alfa-2a alone, lamivudine alone, and the two in combination in patients with HBeAg-negative chronic hepatitis B" N Engl J Med 351(12):1206-1217 (Sep. 16, 2004).

Micco et al., "Differential boosting of innate and adaptive antiviral responses during pegylated-interferon-alpha therapy of chronic hepatitis B" Journal of Hepatology 58:225-233 (2013).

Nayersina et al., "HLA A2 restricted cytotoxic T lymphocyte responses to multiple hepatitis B surface antigen epitopes during hepatitis B virus infection" J Immunol 150:4659-4671 (May 15, 1993).

Op den Brouw et al., "Hepatitis B virus surface antigen impairs myeloid dendritic cell function: a possible immune escape mechanism of hepatitis B virus" Immunol 126:280-289 ( 2008).

Perrillo et al. "Benefits and Risks of Interferon Therapy for Hepatitis B" Hepatology 49:S103-111 ( 2009).

Shi et al., "Hepatitis B virus suppresses the functional interaction between natural killer cells and plasmacytoid dendritic cells" Journal of Viral Hepatitis 19:e26-e33 (2012).

Wieland et al., "Genomic analysis of the host response to hepatitis B virus infection" Proc. Natl. Acad. Sci. U S A 101:6669-6674 ( 2004).

Wieland et al., "Intrahepatic Induction of Alpha/Beta Interferon Eliminates Viral RNA-Containing Capsids in Hepatitis B Virus Transgenic Mice" J. Virol. 74:4165-4173 ( 2000).

Woltman et al., "Hepatitis B virus lacks immune activating capacity, but actively inhibits plasmacytoid dendritic cell function" PLoS ONE 6(1 Suppl 1-14):e15324 (Jan. 2011).

\* cited by examiner

SEQUENCE LISTING

<160> NUMBER OF SEQ ID NOS: 9

<210> SEQ ID NO 1
<211> LENGTH: 19
<212> TYPE: DNA
<213> ORGANISM: Hepatitis B virus

<400> SEQUENCE: 1
ctgtgccttg ggtggcttt                                                  19

<210> SEQ ID NO 2
<211> LENGTH: 24
<212> TYPE: DNA
<213> ORGANISM: Hepatitis B virus

<400> SEQUENCE: 2
aaggaaagaa gtcagaaggc aaaa                                            24

<210> SEQ ID NO 3
<211> LENGTH: 34
<212> TYPE: DNA
<213> ORGANISM: Hepatitis B virus

<400> SEQUENCE: 3
agctccaaat tctttataag ggtcgatgtc catg                                 34

<210> SEQ ID NO 4
<211> LENGTH: 20
<212> TYPE: DNA
<213> ORGANISM: Hepatitis B virus

<400> SEQUENCE: 4
gtgtctgcgg cgttttatca                                                 20

<210> SEQ ID NO 5
<211> LENGTH: 21
<212> TYPE: DNA
<213> ORGANISM: Hepatitis B virus

<400> SEQUENCE: 5
gacaaacggg caacatacct t                                               21

<210> SEQ ID NO 6
<211> LENGTH: 28
<212> TYPE: DNA
<213> ORGANISM: Hepatitis B virus

<400> SEQUENCE: 6
cctctkcatc ctgctgctat gcctcatc                                        28

<210> SEQ ID NO 7
<211> LENGTH: 20
<212> TYPE: DNA
<213> ORGANISM: Hepatitis B virus

<400> SEQUENCE: 7
aagaaaaacc ccgcctgtaa                                                 20

<210> SEQ ID NO 8
<211> LENGTH: 23
<212> TYPE: DNA
<213> ORGANISM: Hepatitis B virus

<400> SEQUENCE: 8

```
cctgttctga ctactgcctc tcc                                               23

<210> SEQ ID NO 9
<211> LENGTH: 27
<212> TYPE: DNA
<213> ORGANISM: Hepatitis B virus

<400> SEQUENCE: 9
cctgatgtga tgttctccat gttcagc                                           27
```

Combination therapy of an HBV capsid assembly inhibitor and an interferon

COMBINATION THERAPY OF AN HBV CAPSID ASSEMBLY INHIBITOR AND AN INTERFERON

RELATED APPLICATIONS

This application is a continuation of International Application No. PCT/EP2016/076195, filed Oct. 31, 2016, which claims priority to Application No. PCT/CN2015/093688, filed Nov. 3, 2015, each of which is incorporated herein by reference in its entirety.

TECHNICAL FIELD

The present invention is directed to compositions and methods for treating hepatitis B virus infection. In particular, the present invention is directed to a combination therapy comprising administration of an HBV capsid assembly inhibitor and an interferon for use in the treatment of hepatitis B virus infections.

SEQUENCE LISTING

This application contains a Sequence Listing which has been submitted via EFS-Web and is hereby incorporated by reference in its entirety. Said ASCII copy, created on Apr. 25, 2018, is named Sequence_Listing.txt and is 1,694 bytes in size.

FIELD OF THE INVENTION

Chronic infection of Hepatitis B virus (HBV) is a serious public health problem, with more than 240 million people chronically infected worldwide. HBV belongs to the Hepadnaviridae family and has an icosahedral core comprising 240 copies of the capsid (or core) protein. The predominant biological function of capsid protein is to act as a structural protein to encapsidate pre-genomic RNA and to form immature capsid particles in the cytoplasm. This step is prerequisite for viral DNA replication. Following entry into hepatocyte, its viral genome is delivered into nucleus where a covalently closed circular DNA (cccDNA) is formed through DNA repair of partially double-stranded viral genome. The cccDNA in turn serves as the template for transcription of viral RNAs. Viral pre-genomic RNA interacts with other two viral components, capsid protein and polymerase to form capsid particles where viral DNA replication occurs. When a near full-length relaxed circular DNA is formed through reverse-transcription of viral pregenomic RNA, an immature capsid becomes a mature capsid. Most copies of the encapsidated genome are efficiently associated with cellular lipids and viral envelope proteins (S, M, and L) for virion assembly and secretion. However, non-infectious particles are also produced that greatly outnumber the infectious virions. These empty, enveloped particles are referred as subviral particles (SVPs). The S, M and L envelope proteins are expressed from a single ORF (open reading frame) that contains three different start codons. All three proteins share a 226aa sequence, the S-domain, at their C-termini. S-domain contains the HBsAg epitope (Lambert, C. & R. Prange. *Virol J*, 2007, 4, 45).

Many observations showed that several HBV viral proteins could counteract the initial host cellular response by interfering with the viral recognition signaling system and subsequently the interferon (IFN) antiviral activity. Among these, the excessive secretion of HBV empty subviral particles may participate to the maintenance of the immunological tolerant state observed in chronically infected patients (CHB). The persistent exposure to HBsAg and other viral antigens can lead to HBV-specific T-cell deletion or to progressive functional impairment (Kondo et al. *Journal of Immunology* 1993, 150, 4659-4671; Kondo et al. *Journal of Medical Virology* 2004, 74, 425-433; Fisicaro et al. *Gastroenterology*, 2010, 138, 682-93;). Moreover HBsAg has been reported to suppress the function of immune cells such as monocytes, dendritic cells (DCs) and natural killer (NK) cells by direct interaction (Op den Brouw et al. *Immunology*, 2009b, 126, 280-9; Woltman et al. *PLoS One*, 2011, 6, e15324; Shi et al. *J Viral Hepat*. 2012, 19, e26-33; Kondo et al. *ISRN Gasteroenterology*, 2013, Article ID 935295).

It has been well studied that HBV capsid protein plays essential roles in HBV replication. Heteroaryldihydropyrimidines or HAP, including compounds named Bay 41-4109, Bay 38-7690 and Bay 39-5493, were discovered in a tissue culture-based screening (Deres K. et al. *Science* 2003, 893). These HAP analogs act as synthetic allosteric activators and are able to induce aberrant capsid formation that leads to degradation of the core protein. HAP analogs also reorganized core protein from preassembled capsids into noncapsid polymers, presumably by interaction of HAP with dimers freed during capsid 'breathing', the transitory breaking of individual inter-subunit bonds. Bay 41-4109 was administered to HBV infected transgenic mouse model or humanized mouse models and demonstrated in vivo efficacy with HBV DNA reduction (Deres K. et al. *Science* 2003, 893; Brezillon N. et al. *PLoS ONE* 2011, e25096).

The other first-line treatment for hepatitis B is IFN-α (interferon alpha), albeit it is limited by its poor, long-term response, and side effects. IFN-α, as a front-line host defense against viral infections, is known to induce interferon-stimulated genes (ISGs), which play a diverse and pleiotropic role in targeting various viral functions at different steps of viral replication cycle, thereby potently suppressing viral infection. In addition, IFN-α has an immunomodulatory effect that can indirectly inhibit HBV replication by affecting cell-mediated immunity in vivo (Micco L., et al., J. Hepatol, 2013, 58, 225-233). Even though IFN-administration has shown to inhibit HBV replication in vitro and in vivo (Christen V., et al., J. Virol. 2007, 81:159-165; Guan S. H., et al., J. Gastroenterol, 2007, 13:228-235; Wieland S. F., et al., J. Virol., 2000, 74, 4165-4173), a large number of individuals, particularly those displaying high viral loads, respond poorly, suggesting that HBV may have evolved mechanisms to antagonize the IFN response, as alluded to earlier. Chronic HBV infection is generally characterized by dysfunctional innate and adaptive immune responses (Boni C., J. Virol., 2007, 81, 4215-4225). For example, in HBV infected chimpanzees, IFN-α, was not induced (Wieland S., et al., Proc. Natl. Acad. Sci. USA, 2004, 101, 6669-6674). When treated with Pegylated IFN-α, the effectiveness of a sustained virological response was achieved in only about 30% of HBeAg-positive and 40% of HBeAg-negative cases in clinical studies (Perrillo R., Hepatology, 2009, 49, S103-111; Janssen H. L., et al., Lancet, 2005, 365, 123-129;Lau G. K., et al., N. Engl. J. Med., 2005, 352, 2682-2695). The antiviral mechanisms of the interferon alpha and the reasons for the differential therapeutic response among the treated patients remain to be elucidated.

HBsAg is a biomarker for prognosis and treatment response in chronic hepatitis B. The standard of clinic cure for HBV infection is the loss and/or seroconversion of HBsAg. However current therapies have demonstrated very low rates of HBsAg clearance, comparable to those observed in placebos (Janssen et al. *Lancet*, 2005, 365, 123-9; Marcellin et al. *N. Engl. J. Med.*, 2004, 351, 1206-17; Buster et al. *Hepatology*, 2007, 46, 388-94). Therefore, a new therapy aiming to increase a success rate of inducing HBsAg loss, and/or HBeAg loss, and/or HBV DNA reduction, and/or HBV clearance and/or seroconversion, and/or normalization of ALT, and/or promoting the production of anti-HBs is greatly in demand of unmet medical need.

SUMMARY OF THE INVENTION

The present invention relates to a pharmaceutical composition comprising an HBV capsid assembly inhibitor and an interferon, in a pharmaceutically acceptable carrier.

The "HBV capsid assembly inhibitor" herein is a compound of formula (I), (II) or (III), or any one of the compounds disclosed in patent WO2014/037480, WO 2014/184328 and WO2015/132276; particularly the "HBV capsid assembly inhibitor" herein is (S)-4-[(R)-6-(2-Chloro-4-fluoro-phenyl)-5-methoxycarbonyl-2-thiazol-2-yl-3,6-dihydro-pyrimidin-4-ylmethyl]-morpholine-3-carboxylic acid; (R)-6-((S)-2-Carboxy-4,4-difluoro-pyrrolidin-1-ylmethyl)-4-(2-chloro-4-fluoro-phenyl)-2-thiazol-2-yl-1,4-dihydro-pyrimidine-5-carboxylic acid methyl ester; (2R,3S)-4-[(R)-6-(2-Chloro-3-fluoro-phenyl)-5-ethoxycarbonyl-2-thiazol-2-yl-3,6-dihydro-pyrimidin-4-ylmethyl]-2-methyl-morpholine-3-carboxylic acid; 2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid; 2-[(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid; 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; 3-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; 4-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-3,3-dimethyl-butanoic acid; (8S,8aR)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid; or (8R,8aS)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid; or pharmaceutically acceptable salt, or enantiomer, or diastereomer thereof.

The "interferon" herein is selected from the group consisting of interferon alpha, peginterferon-alpha 2a, recombinant interferon alpha-2a, interferon alpha-2a, peginterferon alpha-2b, recombinant interferon alpha-2b, interferon alpha-2b, glycosylated interferon alpha-2b, interferon alpha-2b XL, recombinant interferon alpha-2c, interferon alpha-2c, interferon beta, peginterferon beta-1a, interferon beta-1a, interferon delta, peginterferon lambda-1, interferon lambda, interferon omega, interferon tau, gamma interferon, interferon alfacon-1, interferon alpha-n1, interferon alpha-n3, albinterferon alpha-2b, BLX-883, DA-3021, PEG-Infergen, and Belerofon. In one embodiment, the interferon is a y-branched pegylated recombinant human interferon alpha-2b injection (or Pai Ge Bin from Amoytop Biotech). In one embodiment, the interferon is a non-conjugated interferon alfa or a pegylated alfa-type interferon; particularly the interferon is Roferon A, Intron A, Pegasys or PegIntron; more particularly the interferon is Roferon A or Pegasys.

DETAILED DESCRIPTION OF THE INVENTION

Figure 1:
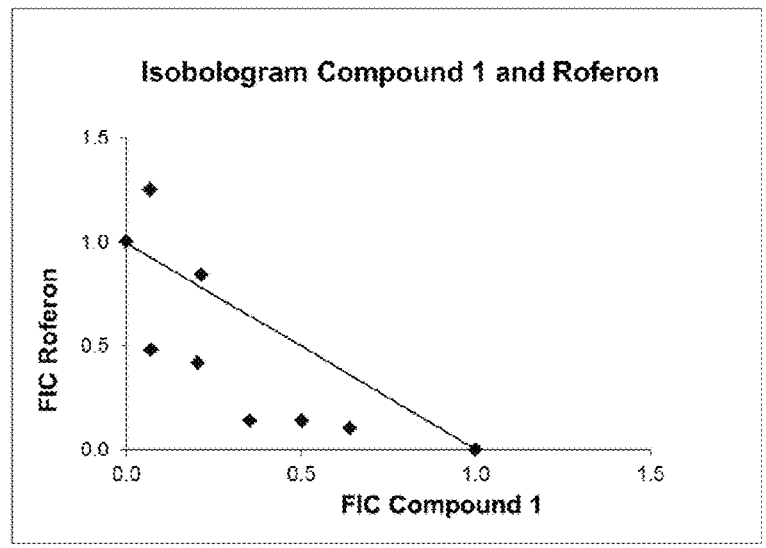
FIG. 1: Isobologram of FIC for the pair-wise checkerboard combination of Roferon and Compound 1 (at the 50% effect level). The diagonal lane connecting points (0, 1) and (1, 0) represents additivity (CI=1). Data points below this lane show synergism, data points above show antagonism. Shown are mean values from 3 independent experiments.

Unless defined otherwise, all technical and scientific terms used herein have the same meaning as commonly understood by one of ordinary skill in the art to which this invention pertains.

As used herein, the term "$C_{1-6}$alkyl" refers to a monovalent linear or branched saturated hydrocarbon group of 1 to 6 carbon atoms. In particular embodiments, $C_{1-6}$alkyl has 1 to 6 carbon atoms, and in more particular embodiments 1 to 4 carbon atoms. Examples of $C_{1-6}$alkyl include methyl, ethyl, propyl, isopropyl, n-butyl, iso-butyl, sec-butyl or tert-butyl.

As used herein, the term "halo" or "halogen" are used interchangeably herein and refer to fluoro, chloro, bromo, or iodo.

The term "haloC$_{1-6}$alkyl" refers to a C$_{1-6}$alkyl group wherein at least one of the hydrogen atoms of the C$_{1-6}$alkyl group has been replaced by same or different halogen atoms, particularly fluoro atoms. Examples of haloC$_{1-6}$alkyl include monofluoro-, difluoro- or trifluoro-methyl, -ethyl or -propyl, for example 3,3,3-trifluoropropyl, 2-fluoroethyl, trifluoroethyl, fluoromethyl, difluoromethyl, difluoroethyl or trifluoromethyl.

As used herein, the term "C$_{1-6}$alkoxy" refers to a group of C$_{1-6}$alkyl-O—, wherein the "C$_{1-6}$alkyl" is as defined above; for example methoxy, ethoxy, propoxy, iso-propoxy, n-butoxy, iso-butoxy, 2-butoxy, tert-butoxy and the like. Particular "C$_{1-6}$alkoxy" groups are methoxy and ethoxy and more particularly methoxy.

As used herein, the term "C$_{3-7}$cycloalkyl" refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "C$_{3-7}$cycloalkyl" groups are cyclopropyl, cyclopentyl and cyclohexyl.

As used herein, the term "heterocyclic" ring or "heterocyclyl" refers to a saturated or partly unsaturated monocyclic or bicyclic ring containing from 3 to 10 ring atoms which can comprise one, two or three atoms selected from nitrogen, oxygen and/or sulfur. Examples of monocyclic heterocyclyl rings containing in particular from 3 to 7 ring atoms include, but not limited to, aziridinyl, azetidinyl, oxetanyl, piperidinyl, piperazinyl, azepinyl, diazepanyl, pyrrolidinyl, morpholinyl, dihydrofuryl, tetrahydrofuryl, tetrahydropyranyl, tetrahydrothiopyranyl and thiomorpholinyl. Bicyclic heterocyclyl can be bicyclic fused ring or bicyclic bridged ring. Examples for bicyclic heterocyclyl are 8-azabicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, 3-thia-9-aza-bicyclo[3.3.1]nonyl, or difluoroazabicyclo[3.2.1]octyl. Monocyclic and bicyclic heterocyclyl can be further substituted by halogen, C$_{1-6}$alkyl, cyano, carboxy, carboxyC$_{1-6}$alkyl.

As used herein, the term "diastereomer" refers to a stereoisomer with two or more centers of chirality and whose molecules are not mirror images of one another. Diastereomers have different physical properties, e.g. melting points, boiling points, spectral properties, activities and reactivities.

As used herein, the term "enantiomers" refers to two stereoisomers of a compound which are non-superimposable mirror images of one another.

As used herein, the term "pharmaceutically acceptable salts" refers to salts which are not biologically or otherwise undesirable. Pharmaceutically acceptable salts include both acid and base addition salts.

As used herein, the term "prodrug" refers to a form or derivative of a compound which is metabolized in vivo, e.g., by biological fluids or enzymes by a subject after administration, into a pharmacologically active form of the compound in order to produce the desired pharmacological effect. Prodrugs are described e.g. in the Organic Chemistry of Drug Design and Drug Action by Richard B. Silverman, Academic Press, San Diego, 2004, Chapter 8 Prodrugs and Drug Delivery Systems, pp. 497-558.

The term "pharmaceutically acceptable acid addition salt" refers to those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" refers to those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

As used herein, "combo" refers to combination.

As used herein, "HBV DNA" refers to DNA material of HBV.

As used herein, "HBsAg" refers to hepatitis B surface antigen.

As used herein, "HBeAg" refers to hepatitis B e antigen.

As used herein, "hepatitis B virus" or "HBV" refers to a member of the Hepadnaviridae family having a small double-stranded DNA genome of approximately 3,200 base pairs and a tropism for liver cells. "HBV" includes hepatitis B virus that infects any of a variety of mammalian (e.g., human, non-human primate, etc.) and avian (duck, etc.) hosts. "HBV" includes any known HBV genotype, e.g., serotype A, B, C, D, E, F, and G; any HBV serotype or HBV subtype; any HBV isolate; HBV variants, e.g., HBeAg-negative variants, drug-resistant HBV variants (e.g., lamivudine-resistant variants; adefovir-resistant mutants; tenofovir-resistant mutants; entecavir-resistant mutants; etc.); and the like.

As used herein, "HBV capsid assembly inhibitor" refers to a compound that inhibits and/or disrupts and/or accelerates and/or hinders and/or delays and or reduces and/or modifies normal HBV capsid assembly (e.g., during maturation) and/or normal capsid disassembly (e.g., during infectivity) and/or perturbs capsid stability, thereby inducing aberrant capsid morphology and function.

The term "therapeutically effective amount" refers to an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgment of the attending medical or veterinary practitioner, and other factors.

The term "interferon" further includes conjugates, for instance interferon alfa (IFN-α) conjugates that can be prepared by coupling an interferon alfa to a water-soluble polymer. A non-limiting list of such polymers includes other polyalkylene oxide homopolymers such as polyethylene glycol (PEG), polypropylene glycols, polyoxyethylenated polyols, copolymers thereof and block copolymers thereof. As an alternative to polyalkylene oxide-based polymers, effectively non-antigenic materials such as dextran, polyvinylpyrrolidones, polyacrylamides, polyvinyl alcohols, carbohydrate-based polymers and the like can be used. Such interferon alfa-polymer conjugates are described in U.S. Pat. Nos. 4,766,106, 4,917,888, European Patent Application No. 0 236 987, European Patent Application Nos. 0510 356, 0 593 868 and 0 809 996 (pegylated interferon alfa-2a) and International Publication No. WO 95/13090.

As used herein the term "pegylated" means covalent conjugates of one or more polyethylene glycol (PEG) molecules and one or more alpha- or beta-type interferon molecules. Preferred conjugates for use in the formulations of the invention have one to four PEG molecules per interferon molecule, and more preferably, the conjugates are between a single PEG molecule and a single interferon molecule. The pegylated interferon may comprise a single positional isomer or a mixture of conjugate positional isomers, e.g, the PEG molecules are covalently attached to different amino acid residues on the individual interferon molecules. For example, U.S. Pat. No. 5,951,974 describes the preparation of mixtures of PEG-interferon alpha conjugate positional isomers in which some of the isomers are conjugates between PEG and a histidine residue of the interferon molecule, other isomers in the mixture are conjugates between PEG and an interferon lysine residue and still other isomers are conjugates between PEG and the amino terminus of the interferon molecule.

The present invention relates to a pharmaceutical composition comprising an HBV capsid assembly inhibitor and an interferon, in a pharmaceutically acceptable carrier.

In one embodiment of the present invention, the "HBV capsid assembly inhibitor" is a compound of formula (I):

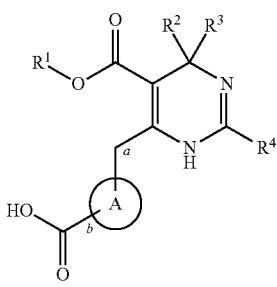

(I)

wherein $R^1$ is $C_{1-6}$alkyl or trifluoromethyl-$C_xH_{2x}$-, wherein x is 1, 2, 3, 4, 5 or 6;

One of $R^2$ and $R^3$ is phenyl, which is once or twice or three times substituted by $C_{1-6}$alkyl, cyano or halogen; and the other one is hydrogen or deuterium;

$R^4$ is phenyl, thiazolyl, oxazolyl, imidazolyl, thienyl or pyridinyl, which is unsubstituted or substituted by $C_{1-6}$alkyl, $C_{1-6}$alkylsulfanyl, halogen or cycloalkyl, wherein $C_{1-6}$alkyl can be further optionally substituted with halogen;

A is

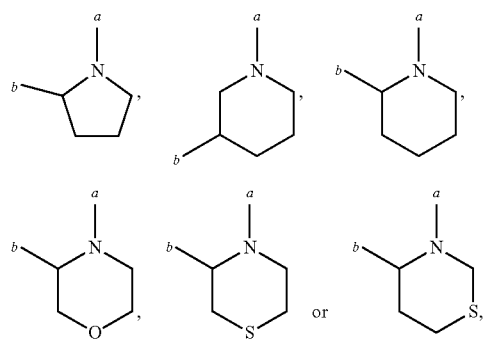

which is unsubstituted or substituted by groups selected from $C_{1-6}$alkyl, deuterium and halogen;

or pharmaceutically acceptable salt, or enantiomer, or diastereomer thereof.

More particularly the HBV capsid assembly inhibitor according to present invention relates to (S)-4-[(R)-6-(2-Chloro-4-fluoro-phenyl)-5-methoxycarbonyl-2-thiazol-2-yl-3,6-dihydro-pyrimidin-4-ylmethyl]-morpholine-3-carboxylic acid; (R)-6-((S)-2-Carboxy-4,4-difluoro-pyrrolidin-1-ylmethyl)-4-(2-chloro-4-fluoro-phenyl)-2-thiazol-2-yl-1,4-dihydro-pyrimidine-5-carboxylic acid methyl ester; or (2R,3S)-4-[(R)-6-(2-Chloro-3-fluoro-phenyl)-5-ethoxycarbonyl-2-thiazol-2-yl-3,6-dihydro-pyrimidin-4-ylmethyl]-2-methyl-morpholine-3-carboxylic acid; or any other compound disclosed in patent WO2014/037480; or pharmaceutically acceptable salt, or enantiomer, or diastereomer thereof. Compounds of formula (I) and compound 1, 2 and 3 can be obtained by the synthetic procedures described in WO2014/037480.

In another embodiment of present invention, the HBV capsid assembly inhibitor is a compound of formula (II):

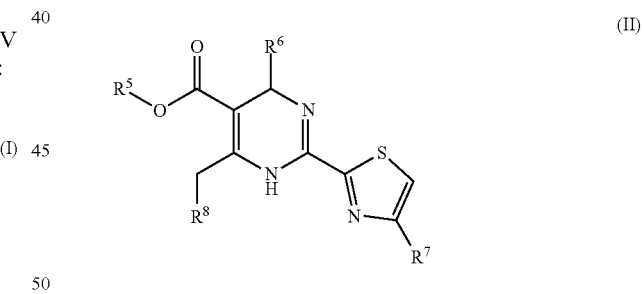

(II)

wherein $R^5$ is $C_{1-6}$alkyl;

$R^6$ is phenyl, which is once or twice or three times substituted by halogen or $C_{1-6}$alkyl;

$R^7$ is hydrogen or $C_{1-6}$alkyl;

$R^8$ is bicyclic bridged heterocyclyl;

or pharmaceutically acceptable salt, or tautomerism isomer, or enantiomer, or diastereomer thereof.

More particularly the HBV capsid assembly inhibitor according to present invention relates to 2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid; or 2-[(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl] acetic acid; or any other compound disclosed in patent WO 2014/184328; or pharmaceutically acceptable salt, or tautomerism isomer, or enantiomer, or diastereomer thereof. Compounds of formula (II) and compound 8 and 9 can be obtained by the synthetic procedures described in WO 2014/184328.

In another embodiment of present invention, the HBV capsid assembly inhibitor is a compound of formula (III):

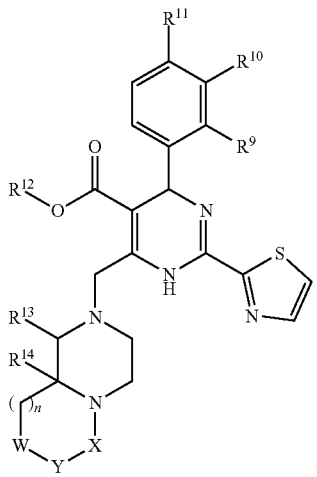
(III)

wherein
$R^9$ is hydrogen, halogen or $C_{1-6}$alkyl;
$R^{10}$ is hydrogen or halogen;
$R^{11}$ is hydrogen or halogen;
$R^{12}$ is $C_{1-6}$alkyl;
$R^{13}$ is hydrogen, hydroxyC$_{1-6}$alkyl, aminocarbonyl, $C_{1-6}$alkoxycarbonyl or carboxy;
$R^{14}$ is hydrogen, $C_{1-6}$alkoxycarbonyl or carboxy-$C_mH_{2m}$-;
X is carbonyl or sulfonyl;
Y is —CH$_2$—, —O— or —N($R^{15}$)—,
  wherein $R^{15}$ is hydrogen, $C_{1-6}$alkyl, haloC$_{1-6}$alkyl, $C_{3-7}$cycloalkyl-$C_mH_{2m}$—, $C_{1-6}$alkoxycarbonyl-$C_mH_{2m}$—, —$C_tH_{2t}$—COOH, -haloC$_{1-6}$alkyl-COOH, -($C_{1-6}$alkoxy)C$_{1-6}$alkyl-COOH, —$C_{1-6}$alkyl-COOH, —$C_{3-7}$cycloalkyl-$C_mH_{2m}$—COOH, —$C_mH_{2m}$-$C_{3-7}$cycloalkyl-COOH, hydroxy-$C_tH_{2t}$—, carboxyspiro[3.3] heptyl or carboxyphenyl-$C_mH_{2m}$—, carboxypyridinyl-$C_mH_{2m}$—;
W is —CH$_2$—, —C(C$_{1-6}$alkyl)$_2$-, —O— or carbonyl;
n is 0 or 1;
m is 0-7;
t is 1-7;
  or pharmaceutically acceptable salt, or enantiomer or diastereomer thereof.
More particularly the HBV capsid assembly inhibitor according to present invention relates to 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; 3-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2yl]-2,2-dimethyl-propanoic acid; 4-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-3,3-dimethyl-butanoic acid; (8S,8aR)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid; or (8R,8aS)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid; or any other compound disclosed in patent WO2015/132276; or pharmaceutically acceptable salt, or enantiomer, or diastereomer thereof. Compounds of formula (III) and compound 4, 5, 6, 7, 10 and 11 can be obtained by the synthetic procedures described in WO2015/132276.

In another embodiment of present invention, the HBV capsid assembly inhibitor used in the combination with interferon is any compound selected from patent WO2008154817, WO2008154819, WO2014029193, WO2015074546, CN103664897 and CN103664925.

Suitable interferons in accordance with the present invention may be any naturally-occurring or recombinant interferon alfa, beta or gamma known to those skilled in the art. Natural and recombinant alfa-interferons that may be used include interferon alfa-n1 (e.g., Surniferon®, Surnitomo®)), interferon alfa-n3, interferon alfa-2a (Roferon A®, Hoffmann-La Roche, Inc.) interferon alfa-2b (Intron A®, Schering-Plough Corp.), interferon alfa-2c (Berofor®, Boehringer Ingelheim, Inc.), and consensus interferon (Infergen®, InterMune, Inc.). Preferred interferons are interferon alfa-2a and interferon alfa-2b.

In one embodiment of the present invention, suitable interferons in accordance with the present invention include, but are not limited to, recombinant interferon alfa-2b such as Intron A®; recombinant interferon alfa-2a such as Roferon A®; recombinant interferon beta-1b such as Betaferon®; recombinant interferon beta-1a such as Avonex® and Rebf®; and recombinant interferon gamma-1b such as Imukin®. The use of recombinant interferon alfa-2a or alfa-2b is preferred.

The terms "interferon alfa-2a", "interferon alfa-2b" and "interferon beta-1a" are further intended to include "pegylated" analogs meaning polyethylene glycol modified conjugates of interferon alfa-2a such as Pegasys®, interferon alfa-2b such as PegIntron® and interferon beta-1a such as Plegridy®. The use of pegylated recombinant interferon alfa-2a or alfa 2b is preferred.

In one embodiment of the present invention, the "interferon" is a non-conjugated interferon alfa or a pegylated conjugate thereof.

More specifically, the "interferon" is selected from the group consisting of interferon alfa-2a such as Roferon A®, interferon alfa-2b such as Intron A®, pegylated interferon alfa-2a such as Pegasys® and pegylated interferon alfa-2b such as PegIntron® respectively.

Obtaining and isolating interferon alfa from natural or recombinant sources is well known (Pestka, Arch. Biochem. Biophys. 221, 1 (1983); European Pat. No. 043980.

Further more specifically, the "interferon" is a non-conjugated interferon alfa-2a (for instance Roferon A®) or a pegylated alfa-type interferon (for instance Pegasys®):

In yet another embodiment the above pegylated alfa-type interferon is an alfa-2a interferon.

In one embodiment of the present invention, the pharmaceutical composition comprises an HBV capsid assembly inhibitor and an interferon, wherein the HBV capsid assembly inhibitor and the interferon are independently selected from Table 1.

TABLE 1

| Compound NO. | Class | Compound Name | Compound Structure | Disclosed in Patent |
|---|---|---|---|---|
| 1 | HBV capsid assembly inhibitor | (S)-4-[(R)-6-(2-Chloro-4-fluoro-phenyl)-5-methoxycarbonyl-2-thiazol-2-yl-3,6-dihydro-pyrimidin-4-ylmethyl]-morpholine-3-carboxylic acid | 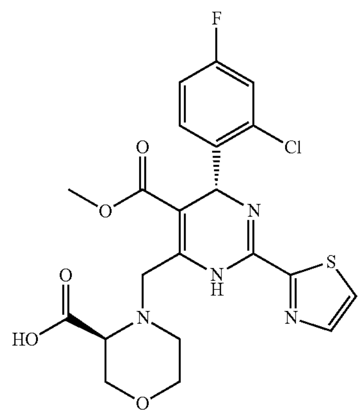 [SMILES: COC(=O)C1=C(CN2CCOC[C@H]2C(=O)O)NC(c2nccs2)=N[C@H]1c1ccc(F)cc1Cl] | WO 2014/037480 |
| 2 | HBV capsid assembly inhibitor | (R)-6-((S)-2-Carboxy-4,4-difluoro-pyrrolidin-1-ylmethyl)-4-(2-chloro-4-fluoro-phenyl)-2-thiazol-2-yl-1,4-dihydro-pyrimidine-5-carboxylic acid methyl ester | 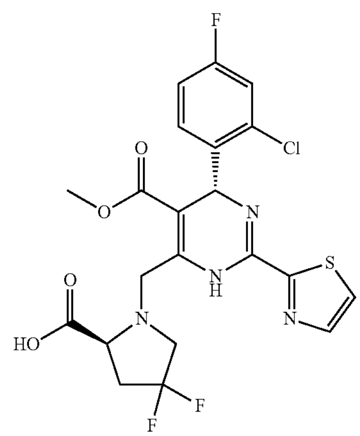 [SMILES: COC(=O)C1=C(CN2CC(F)(F)C[C@H]2C(=O)O)NC(c2nccs2)=N[C@H]1c1ccc(F)cc1Cl] | WO 2014/037480 |
| 3 | HBV capsid assembly inhitor | (2R,3S)-4-[(R)-6-(2-Chloro-3-fluoro-phenyl)-5-ethoxycarbonyl-2-thiazol-2-yl-3,6-dihydro-pyrimidin-4-ylmethyl]-2-methyl-morpholine-3-carboxylic acid | 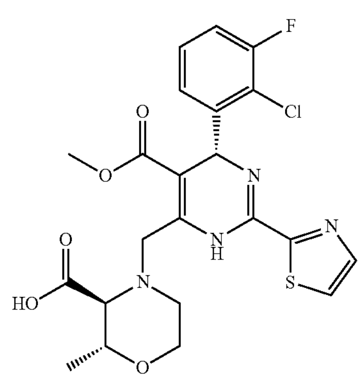 [SMILES: COC(=O)C1=C(CN2CCO[C@H](C)[C@H]2C(=O)O)NC(c2nccs2)=N[C@H]1c1cccc(F)c1Cl] | WO 2014/037480 |

TABLE 1-continued

List of HBV capsid assembly inhibitors and interferons

| Compound NO. | Class | Compound Name | Compound Structure | Disclosed in Patent |
|---|---|---|---|---|
| 4 | HBV capsid assembly inhibitor | 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid | 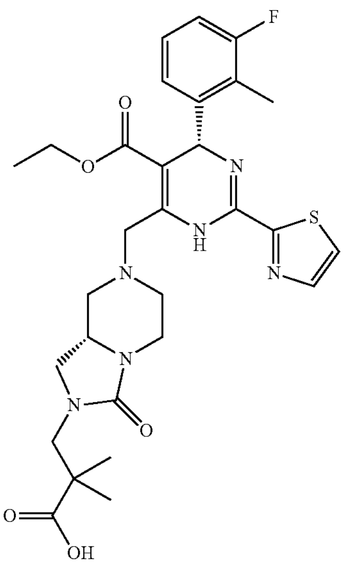 [SMILES: CCOC(=O)C1=C(CN2CCN3C(=O)N(CC(C)(C)C(=O)O)C[C@@H]3C2)NC(c2nccs2)=N[C@H]1c1cccc(F)c1C] | WO 2015/132276 |
| 5 | HBV capsid assembly inhibitor | 3-[(8aS)-7-[[(4R)-4-(2-chloro-4-fluorr-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid | 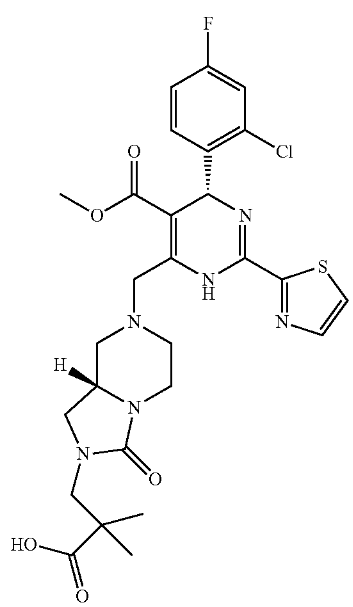 [SMILES: COC(=O)C1=C(CN2CCN3C(=O)N(CC(C)(C)C(=O)O)C[C@@H]3C2)NC(c2nccs2)=N[C@H]1c1ccc(F)cc1Cl] | WO 2015/132276 |

TABLE 1-continued

List of HBV capsid assembly inhibitors and interferons

| Compound NO. | Class | Compound Name | Compound Structure | Disclosed in Patent |
|---|---|---|---|---|
| 6 | HBV capsid assembly inhibitor | 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid | 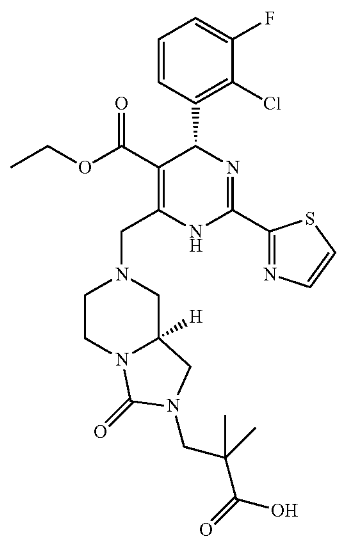 [SMILES: CCOC(=O)C1=C(CN2CCN3C(=O)N(CC(C)(C)C(=O)O)C[C@@H]3C2)NC(c2nccs2)=N[C@H]1c1cccc(F)c1Cl] | WO 2015/132276 |
| 7 | HBV capsid assembly inhibitor | 4-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-3,3-dimethyl-butanoic acid | 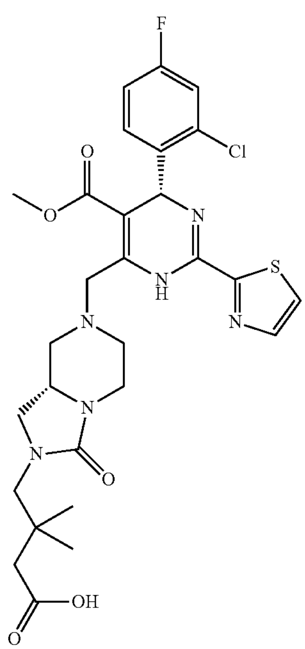 [SMILES: COC(=O)C1=C(CN2CCN3C(=O)N(CC(C)(C)CC(=O)O)C[C@@H]3C2)NC(c2nccs2)=N[C@H]1c1ccc(F)cc1Cl] | WO 2015/132276 |

TABLE 1-continued

List of HBV capsid assembly inhibitors and interferons

| Compound NO. | Class | Compound Name | Compound Structure | Disclosed in Patent |
|---|---|---|---|---|
| 8 | HBV capsid assembly inhibitor | 2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid | 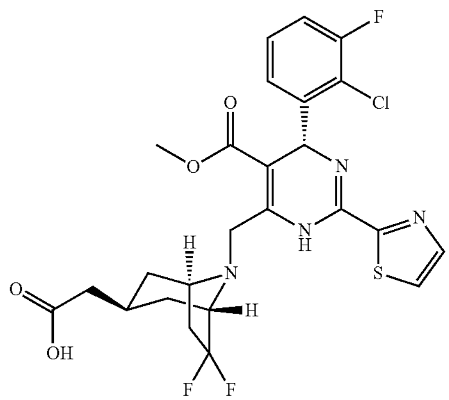 [SMILES: COC(=O)C1=C(CN2[C@@H]3C[C@H](CC(=O)O)C[C@H]2C(F)(F)C3)NC(c2nccs2)=N[C@H]1c1cccc(F)c1Cl] | WO 2014/184328 |
| 9 | HBV capsid assembly inhibitor | 2-[(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid | 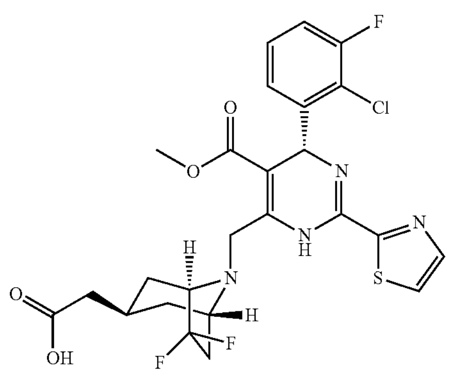 [SMILES: COC(=O)C1=C(CN2[C@H]3C[C@@H](CC(=O)O)C[C@@H]2C(F)(F)C3)NC(c2nccs2)=N[C@H]1c1cccc(F)c1Cl] | WO 2014/184328 |
| 10 | HBV capsid assembly inhibitor | (8S,8aR)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid | 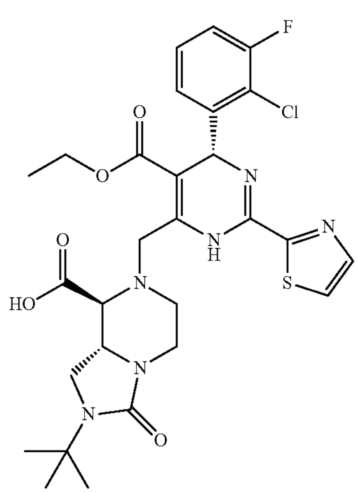 [SMILES: CCOC(=O)C1=C(CN2CCN3C(=O)N(C(C)(C)C)C[C@@H]3[C@H]2C(=O)O)NC(c2nccs2)=N[C@H]1c1cccc(F)c1Cl] | WO 2015/132276 |

TABLE 1-continued

List of HBV capsid assembly inhibitors and interferons

| Compound NO. | Class | Compound Name | Compound Structure | Disclosed in Patent |
|---|---|---|---|---|
| 11 | HBV capsid assembly inhibitor | (8R,8aS)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid | 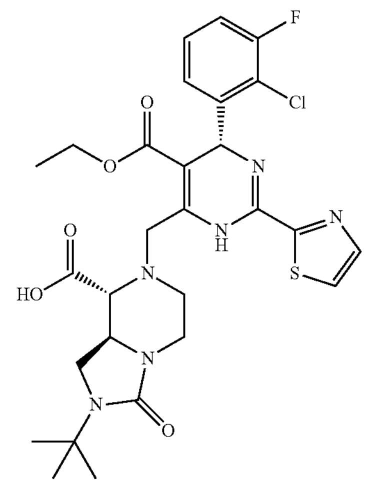 [SMILES: CCOC(=O)C1=C(CN2CCN3C(=O)N(C(C)(C)C)C[C@H]3[C@@H]2C(=O)O)NC(c2nccs2)=N[C@H]1c1cccc(F)c1Cl] | WO 2015/132276 |
| 12 | IFN | interferon alfa-2a (Roferon A ®) | | |
| 13 | IFN | interferon alfa-2b (Intron A ®) | | |
| 14 | IFN | pegylated interferon alfa-2a (Pegasys ®) | | |
| 15 | IFN | pegylated interferon alfa-2b (Pegintron ®) | | |

More particularly, the present invention relates to a pharmaceutical composition comprising an HBV capsid assembly inhibitor and an interferon which is selected from any one of the following combinations:

Compound 1 and Compound 12; Compound 2 and Compound 12;
Compound 3 and Compound 12; Compound 4 and Compound 12;
Compound 5 and Compound 12; Compound 6 and Compound 12;
Compound 7 and Compound 12; Compound 8 and Compound 12;
Compound 9 and Compound 12; Compound 10 and Compound 12;
Compound 11 and Compound 12; Compound 1 and Compound 13;
Compound 2 and Compound 13; Compound 3 and Compound 13;
Compound 4 and Compound 13; Compound 5 and Compound 13;
Compound 6 and Compound 13; Compound 7 and Compound 13;
Compound 8 and Compound 13; Compound 9 and Compound 13;
Compound 10 and Compound 13; Compound 11 and Compound 13;
Compound 1 and Compound 14; Compound 2 and Compound 14;
Compound 3 and Compound 14; Compound 4 and Compound 14;
Compound 5 and Compound 14; Compound 6 and Compound 14;
Compound 7 and Compound 14; Compound 8 and Compound 14;
Compound 9 and Compound 14; Compound 10 and Compound 14;
Compound 11 and Compound 14; Compound 1 and Compound 15;
Compound 2 and Compound 15; Compound 3 and Compound 15;
Compound 4 and Compound 15; Compound 5 and Compound 15;
Compound 6 and Compound 15; Compound 7 and Compound 15;
Compound 8 and Compound 15; Compound 9 and Compound 15;
Compound 10 and Compound 15; Compound 11 and Compound 15;
in a pharmaceutically acceptable carrier.

The Compound 1 to 11 of the above said combination can be replaced by its corresponding pharmaceutically acceptable salt, enantiomer or diastereomer, which is another aspect of this invention.

More specifically, the present invention relates to a pharmaceutical composition comprising an HBV capsid assembly inhibitor and an interferon which is selected from any one of the following combinations:
(S)-4-[(R)-6-(2-Chloro-4-fluoro-phenyl)-5-methoxycarbonyl-2-thiazol-2-yl-3,6-dihydro-pyrimidin-4-ylmethyl]-morpholine-3-carboxylic acid and Roferon A;
(R)-6-(S)-2-Carboxy-4,4-difluoro-pyrrolidin-1-ylmethyl)-4-(2-chloro-4-fluoro-phenyl)-2-thiazol-2-yl-1,4-dihydropyrimidine-5-carboxylic acid methyl ester and Roferon A;
(2R,3S)-4-[(R)-6-(2-Chloro-3-fluoro-phenyl)-5-ethoxycarbonyl-2-thiazol-2-yl-3,6-dihydro-pyrimidin-4-ylmethyl]-2-methyl-morpholine-3-carboxylic acid and Roferon A;
3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid and Roferon A;
3-[(8aS)-7-[[(4R)-4-(2-chloro-4-fluoro-phenyl)-5-methoxycarbonyl-2-thiazol-2-yl-1,4-dihydropyrimidin-6-yl]

methyl]-3-oxo-5,6,8,8a-tetrahydro-1H-imidazo[1,5-a]
pyrazin-2-yl]-2,2-dimethyl-propanoic acid and Roferon A;
3-[(8aS)-7-[[(4R)-4-(2-chloro-3-fluoro-phenyl)-5-ethoxycarbonyl-2-thiazol-2-yl-1,4-dihydropyrimidin-6-yl]
methyl]-3-oxo-5,6,8,8a-tetrahydro-1H-imidazo[1,5-a]
pyrazin-2-yl]-2,2-dimethyl-propanoic acid and Roferon A;
4-[(8aS)-7-[[(4R)-4-(2-chloro-4-fluoro-phenyl)-5-methoxycarbonyl-2-thiazol-2-yl-1,4-dihydropyrimidin-6-yl]
methyl]-3-oxo-5,6,8,8a-tetrahydro-1H-imidazo[1,5-a]
pyrazin-2-yl]-3,3-dimethyl-butanoic acid and Roferon A;
2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]
acetic acid and Roferon A;
2-[(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]
acetic acid and Roferon A;
(8S,8aR)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo
[1,5-a]pyrazine-8-carboxylic acid and Roferon A;
(8R,8aS)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo
[1,5-a]pyrazine-8-carboxylic acid and Roferon A;
(S)-4-[(R)-6-(2-Chloro-4-fluoro-phenyl)-5-methoxycarbonyl-2-thiazol-2-yl-3,6-dihydro-pyrimidin-4-ylmethyl]-
morpholine-3-carboxylic acid and Intron A;
(R)-6-(S)-2-Carboxy-4,4-difluoro-pyrrolidin-1-ylmethyl)-
4-(2-chloro-4-fluoro-phenyl)-2-thiazol-2-yl-1,4-dihydropyrimidine-5-carboxylic acid methyl ester and Intron A;
(2R,3S)-4-[(R)-6-(2-Chloro-3-fluoro-phenyl)-5-ethoxycarbonyl-2-thiazol-2-yl-3,6-dihydro-pyrimidin-4-ylmethyl]-
2-methyl-morpholine-3-carboxylic acid and Intron A;
3-[(8aS)-7-[[(4S)-5-ethoxycarbonyl-4-(3-fluoro-2-methylphenyl)-2-thiazol-2-yl-1,4-dihydropyrimidin-6-yl]
methyl]-3-oxo-5,6,8,8a-tetrahydro-1H-imidazo[1,5-a]
pyrazin-2-yl]-2,2-dimethyl-propanoic acid and Intron A;
3-[(8aS)-7-[[(4R)-4-(2-chloro-4-fluoro-phenyl)-5-methoxycarbonyl-2-thiazol-2-yl-1,4-dihydropyrimidin-6-yl]
methyl]-3-oxo-5,6,8,8a-tetrahydro-1H-imidazo[1,5-a]
pyrazin-2-yl]-2,2-dimethyl-propanoic acid and Intron A;
3-[(8aS)-7-[[(4R)-4-(2-chloro-3-fluoro-phenyl)-5-ethoxycarbonyl-2-thiazol-2-yl-1,4-dihydropyrimidin-6-yl]
methyl]-3-oxo-5,6,8,8a-tetrahydro-1H-imidazo[1,5-a]
pyrazin-2-yl]-2,2-dimethyl-propanoic acid and Intron A;
4-[(8aS)-7-[[(4R)-4-(2-chloro-4-fluoro-phenyl)-5-methoxycarbonyl-2-thiazol-2-yl-1,4-dihydropyrimidin-6-yl]
methyl]-3-oxo-5,6,8,8a-tetrahydro-1H-imidazo[1,5-a]
pyrazin-2-yl]-3,3-dimethyl-butanoic acid and Intron A;
2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]
acetic acid and Intron A;
2-[(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]
acetic acid and Intron A;
(8S,8aR)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo
[1,5-a]pyrazine-8-carboxylic acid and Intron A;
(8R,8aS)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo
[1,5-a]pyrazine-8-carboxylic acid and Intron A;
(S)-4-[(R)-6-(2-Chloro-4-fluoro-phenyl)-5-methoxycarbonyl-2-thiazol-2-yl-3,6-dihydro-pyrimidin-4-ylmethyl]-
morpholine-3-carboxylic acid and Pegasys;
(R)-6-(S)-2-Carboxy-4,4-difluoro-pyrrolidin-1-ylmethyl)-
4-(2-chloro-4-fluoro-phenyl)-2-thiazol-2-yl-1,4-dihydropyrimidine-5-carboxylic acid methyl ester and Pegasys;
(2R,3S)-4-[(R)-6-(2-Chloro-3-fluoro-phenyl)-5-ethoxycarbonyl-2-thiazol-2-yl-3,6-dihydro-pyrimidin-4-ylmethyl]-
2-methyl-morpholine-3-carboxylic acid and Pegasys;
3-[(8aS)-7-[[(4S)-5-ethoxycarbonyl-4-(3-fluoro-2-methylphenyl)-2-thiazol-2-yl-1,4-dihydropyrimidin-6-yl]
methyl]-3-oxo-5,6,8,8a-tetrahydro-1H-imidazo[1,5-a]
pyrazin-2-yl]-2,2-dimethyl-propanoic acid and Pegasys;
3-[(8aS)-7-[[(4R)-4-(2-chloro-4-fluoro-phenyl)-5-methoxycarbonyl-2-thiazol-2-yl-1,4-dihydropyrimidin-6-yl]
methyl]-3-oxo-5,6,8,8a-tetrahydro-1H-imidazo[1,5-a]
pyrazin-2-yl]-2,2-dimethyl-propanoic acid and Pegasys;
3-[(8aS)-7-[[(4R)-4-(2-chloro-3-fluoro-phenyl)-5-ethoxycarbonyl-2-thiazol-2-yl-1,4-dihydropyrimidin-6-yl]
methyl]-3-oxo-5,6,8,8a-tetrahydro-1H-imidazo[1,5-a]
pyrazin-2-yl]-2,2-dimethyl-propanoic acid and Pegasys;
4-[(8aS)-7-[[(4R)-4-(2-chloro-4-fluoro-phenyl)-5-methoxycarbonyl-2-thiazol-2-yl-1,4-dihydropyrimidin-6-yl]
methyl]-3-oxo-5,6,8,8a-tetrahydro-1H-imidazo[1,5-a]
pyrazin-2-yl]-3,3-dimethyl-butanoic acid and Pegasys;
2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]
acetic acid and Pegasys;
2-[(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]
acetic acid and Pegasys;
(8S,8aR)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo
[1,5-a]pyrazine-8-carboxylic acid and Pegasys;
(8R,8aS)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo
[1,5-a]pyrazine-8-carboxylic acid and Pegasys;
(S)-4-[(R)-6-(2-Chloro-4-fluoro-phenyl)-5-methoxycarbonyl-2-thiazol-2-yl-3,6-dihydro-pyrimidin-4-ylmethyl]-
morpholine-3-carboxylic acid and PegIntron;
(R)-6-(S)-2-Carboxy-4,4-difluoro-pyrrolidin-1-ylmethyl)-
4-(2-chloro-4-fluoro-phenyl)-2-thiazol-2-yl-1,4-dihydropyrimidine-5-carboxylic acid methyl ester and PegIntron;
(2R,3S)-4-[(R)-6-(2-Chloro-3-fluoro-phenyl)-5-ethoxycarbonyl-2-thiazol-2-yl-3,6-dihydro-pyrimidin-4-ylmethyl]-
2-methyl-morpholine-3-carboxylic acid and PegIntron;
3-[(8aS)-7-[[(4S)-5-ethoxycarbonyl-4-(3-fluoro-2-methylphenyl)-2-thiazol-2-yl-1,4-dihydropyrimidin-6-yl]
methyl]-3-oxo-5,6,8,8a-tetrahydro-1H-imidazo[1,5-a]
pyrazin-2-yl]-2,2-dimethyl-propanoic acid and PegIntron;
3-[(8aS)-7-[[(4R)-4-(2-chloro-4-fluoro-phenyl)-5-methoxycarbonyl-2-thiazol-2-yl-1,4-dihydropyrimidin-6-yl]
methyl]-3-oxo-5,6,8,8a-tetrahydro-1H-imidazo[1,5-a]
pyrazin-2-yl]-2,2-dimethyl-propanoic acid and PegIntron;
3-[(8aS)-7-[[(4R)-4-(2-chloro-3-fluoro-phenyl)-5-ethoxycarbonyl-2-thiazol-2-yl-1,4-dihydropyrimidin-6-yl]
methyl]-3-oxo-5,6,8,8a-tetrahydro-1H-imidazo[1,5-a]
pyrazin-2-yl]-2,2-dimethyl-propanoic acid and PegIntron;

4-[(8aS)-7-[[(4R)-4-(2-chloro-4-fluoro-phenyl)-5-methoxy-carbonyl-2-thiazol-2-yl-1,4-dihydropyrimidin-6-yl]methyl]-3-oxo-5,6,8,8a-tetrahydro-1H-imidazo[1,5-a]pyrazin-2-yl]-3,3-dimethyl-butanoic acid and PegIntron;

2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl] acetic acid and PegIntron;

2-[(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl] acetic acid and PegIntron;

(8S,8aR)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid and PegIntron; or (8R,8aS)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid and PegIntron;

in a pharmaceutically acceptable carrier.

In one embodiment of the present invention, the pharmaceutical composition consists of an HBV capsid assembly inhibitor and an interferon, in a pharmaceutically acceptable carrier. More particularly, the composition consists of:

(S)-4-[(R)-6-(2-Chloro-4-fluoro-phenyl)-5-methoxycarbonyl-2-thiazol-2-yl-3,6-dihydro-pyrimidin-4-ylmethyl]-morpholine-3-carboxylic acid and Roferon A;

3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid and Roferon A;

3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid and Pegasys; or (2R,3S)-4-[(R)-6-(2-Chloro-3-fluoro-phenyl)-5-ethoxycarbonyl-2-thiazol-2-yl-3,6-dihydro-pyrimidin-4-ylmethyl]-2-methyl-morpholine-3-carboxylic acid and Pegasys;

in a pharmaceutically acceptable carrier.

In another embodiment of the present invention, other interferons or HBV capsid assembly inhibitors can also be used in the pharmaceutical composition including small molecules or large molecules. Examples of other HBV capsid assembly inhibitors include, but not limited to, Bay 41-4109, Bay 38-7690, Bay 39-5493, GLS4, AT-61 and AT-130. Examples of other interferons include, but not limited to, Surniferon, Sumitomo, Berofor, Infergen, Multiferon, Rebif, Avonex, Cinnovex, Betaseron/Betaferon, Imukin, Plegridy, Actimmune, Reiferon Retard and Pegetron.

Typical dosages of an HBV capsid assembly inhibitor and/or an interferon can be in the ranges recommended by the manufacturer, and where indicated by in vitro responses in an animal models, can be reduced by up to about one order of magnitude concentration or amount. Thus, the actual dosage will depend upon the judgment of the physician, the condition of the patient, and the effectiveness of the therapeutic method based on the in vitro responsiveness of the appropriate animal models.

Another embodiment of present invention relates to a method for manufacturing a medicament for treatment or prophylaxis of hepatitis B virus infection, characterized in that an HBV capsid assembly inhibitor and an interferon are used in the medicament.

A further embodiment of present invention relates to the method for manufacturing a medicament for treatment or prophylaxis of hepatitis B virus infection, characterized in that the HBV capsid assembly inhibitor and the interferon are co-administered in the same formulation or different formulation.

For purposes of the present invention, "co-administer" refers to any administration of the HBV capsid assembly inhibitor and interferon as the two active agents, either separately or together, where the two active agents are administered as part of an appropriate dose regimen designed to obtain the benefit of the combination therapy. Thus, the two active agents can be administered either as part of the same pharmaceutical composition or in separate pharmaceutical compositions. Also, the two active agents can be administered either at the same time, or sequentially.

The pharmaceutical composition of the HBV capsid assembly inhibitor and interferon can be administered with various pharmaceutically acceptable inert carriers in the form of tablets, capsules, lozengens, troches, hard candies, powders, sprays, creams, salves, suppositories, jellies, gels, pastes, lotions, ointments, elixirs, syrups, and the like. Administration of such dosage forms can be carried out in single or multiple doses. Carries include solid diluents of fillers, sterile aqueous media and various non-toxic organic solvents. Administration of such dosage forms can be carried out through, but not limited to, oral administration, parenteral administration, veterinary administration.

A further embodiment of present invention relates to the method for manufacturing a medicament for treatment or prophylaxis of hepatitis B virus infection, characterized in that the HBV capsid assembly inhibitor and interferon are intended for administration to a subject by the same route or different routes.

A further embodiment of present invention relates to the method for manufacturing a medicament for treatment or prophylaxis of hepatitis B virus infection, characterized in that the HBV capsid assembly inhibitor and interferon thereof are intended for administration to a subject by parenteral or oral administration.

A further embodiment of present invention relates to the method for manufacturing a medicament for treatment or prophylaxis of hepatitis B virus infection, characterized in that the administration of the HBV capsid assembly inhibitor and interferon thereof to a subject is simultaneous or sequential. In any of the methods of the present invention, the administration of agents simultaneously can be performed by separately or sequentially administering agents at the same time, or together as a fixed combination. Also, in any of the methods of the present invention, the administration of agents separately or sequentially can be in any order.

Another embodiment of present invention relates to the method for manufacturing a medicament of composition for treatment or prophylaxis of hepatitis B virus infection, characterized in that HBV capsid assembly inhibitor thereof is a compound of formula (I), formula (II) or formula (III), or pharmaceutically acceptable salt, enantiomer or diastereomer thereof. Particularly, the HBV capsid assembly inhibitor thereof is (S)-4-[(R)-6-(2-Chloro-4-fluoro-phenyl)-5-methoxycarbonyl-2-thiazol-2-yl-3,6-dihydro-pyrimidin-4-ylmethyl]-morpholine-3-carboxylic acid; (R)-6-((S)-2-Carboxy-4,4-difluoro-pyrrolidin-1-ylmethyl)-4-(2-chloro-4-fluoro-phenyl)-2-thiazol-2-yl-1,4-dihydro-pyrimidine-5-carboxylic acid methyl ester; (2R,3S)-4-[(R)-6-(2-Chloro-3-fluoro-phenyl)-5-ethoxycarbonyl-2-thiazol-2-yl-3,6-dihydro-pyrimidin-4-ylmethyl]-2-methyl-morpholine-3-carboxylic acid; 2-[(1R,3S,5S)-8-[[(4R)-4-(2- chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid; 2-[(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid; 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; 3-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; 4-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-3,3-dimethyl-butanoic acid; (8S,8aR)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid; or (8R,8aS)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid; or pharmaceutically acceptable salt, or enantiomer, or diastereomer thereof.

Another embodiment of present invention relates to the method for manufacturing a medicament for treatment or prophylaxis of hepatitis B virus infection, characterized in that the interferon thereof is a non-conjugated interferon alfa or a pegylated alfa-type interferon; particularly the interferon is Roferon A, Intron A, Pegasys or PegIntron; more particularly the interferon is Roferon A or Pegasys.

Another embodiment of present invention relates to the method for manufacturing a medicament for treatment or prophylaxis of hepatitis B virus infection, characterized in that the HBV capsid assembly inhibitor and the interferon used in the medicament are (S)-4-[(R)-6-(2-Chloro-4-fluoro-phenyl)-5-methoxycarbonyl-2-thiazol-2-yl-3,6-dihydro-pyrimidin-4-ylmethyl]-morpholine-3-carboxylic acid and Roferon A; 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid and Roferon A; 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid and Pegasys; or (2R,3S)-4-[(R)-6-(2-Chloro-3-fluoro-phenyl)-5-ethoxycarbonyl-2-thiazol-2-yl-3,6-dihydro-pyrimidin-4-ylmethyl]-2-methyl-morpholine-3-carboxylic acid and Pegasys; in a pharmaceutically acceptable carrier.

Another embodiment of present invention relates to a kit comprising a container comprising an HBV capsid assembly inhibitor and an interferon, said kit can further comprise a sterile diluent.

A further embodiment of present invention relates to the said kit, wherein the kit can further comprise a package insert comprising printed instructions directing the use of a combined treatment of an HBV capsid assembly inhibitor and an interferon as a method for treatment or prophylaxis of hepatitis B virus infection.

Another embodiment of present invention relates to the said kit, wherein the HBV capsid assembly inhibitor is (S)-4-[(R)-6-(2-Chloro-4-fluoro-phenyl)-5-methoxycarbonyl-2-thiazol-2-yl-3,6-dihydro-pyrimidin-4-ylmethyl]-morpholine-3-carboxylic acid; (R)-6-((S)-2-Carboxy-4,4-difluoro-pyrrolidin-1-ylmethyl)-4-(2-chloro-4-fluoro-phenyl)-2-thiazol-2-yl-1,4-dihydro-pyrimidine-5-carboxylic acid methyl ester; (2R,3S)-4-[(R)-6-(2-Chloro-3-fluoro-phenyl)-5-ethoxycarbonyl-2-thiazol-2-yl-3,6-dihydro-pyrimidin-4-ylmethyl]-2-methyl-morpholine-3-carboxylic acid; 2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid; 2-[(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid; 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; 3-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; 4-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-3,3-dimethyl-butanoic acid; (8S,8aR)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid; or (8R,8aS)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid; or pharmaceutically acceptable salt, or enantiomer, or diastereomer thereof.

Another embodiment of present invention relates to the said kit, characterized in that the interferon thereof is a non-conjugated interferon alfa or a pegylated alfa-type interferon; particularly the interferon is Roferon A, Intron A, Pegasys or PegIntron; more particularly the interferon is Roferon A or Pegasys.

Another embodiment of present invention relates to the said kit, characterized in that the HBV capsid assembly inhibitor and the interferon used in the container are: (S)-4-[(R)-6-(2-Chloro-4-fluoro-phenyl)-5-methoxycarbonyl-2-thiazol-2-yl-3,6-dihydro-pyrimidin-4-ylmethyl]-morpholine-3-carboxylic acid and Roferon A; 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid and Roferon A; 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid and Pegasys; or (2R,3S)-4-[(R)-6-(2-Chloro-3-fluoro-phenyl)-5-ethoxycarbonyl-2-thiazol-2-yl-3,6-dihydro-pyrimidin-4-ylmethyl]-2-methyl-morpholine-3-carboxylic acid and Pegasys; in a pharmaceutically acceptable carrier. Another embodiment of present invention relates to a method for the treatment or prophylaxis of hepatitis B virus infection, comprising administration to a subject with an effective first amount of an HBV capsid assembly inhibitor, or pharmaceutically acceptable salt, enantiomer or diastereomer thereof; and a second amount of an interferon; wherein the HBV capsid assembly inhibitor is (S)-4-[(R)-6-(2-Chloro-4-fluoro-phenyl)-5-methoxycarbonyl-2-thiazol-2-yl-3,6-dihydro-pyrimidin-4-ylmethyl]-morpholine-3-carboxylic acid; (R)-6-((S)-2-Carboxy-4,4-difluoro-pyrrolidin-1-ylmethyl)-4-(2-chloro-4-fluoro-phenyl)-2-thiazol-2-yl-1,4-dihydro-pyrimidine-5-carboxylic acid methyl ester; (2R,3S)-4-[(R)-6-(2-Chloro-3-fluoro-phenyl)-5-ethoxycarbonyl-2-thiazol-2-yl-3,6-dihydro-pyrimidin-4-ylmethyl]-2-methyl-morpholine-3-carboxylic acid; 2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid; 2-[(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid; 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; 3-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid; 4-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-3,3-dimethyl-butanoic acid; (8S,8aR)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid; or (8R,8aS)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid; or pharmaceutically acceptable salt, or enantiomer, or diastereomer thereof.

Another embodiment of present invention relates to a method for the treatment or prophylaxis of hepatitis B virus infection, comprising administration to a subject with an effective first amount of an HBV capsid assembly inhibitor, or pharmaceutically acceptable salt, enantiomer or diastereomer thereof; and a second amount of an interferon; wherein the interferon thereof is a non-conjugated interferon alfa or a pegylated alfa-type interferon; particularly the interferon is Roferon A, Intron A, Pegasys or PegIntron; more particularly the interferon is Roferon A or Pegasys.

Another embodiment of present invention relates to a method for the treatment or prophylaxis of hepatitis B virus infection, wherein the HBV capsid assembly inhibitor and the interferon used in the subject are (S)-4-[(R)-6-(2-Chloro-4-fluoro-phenyl)-5-methoxycarbonyl-2-thiazol-2-yl-3,6-dihydro-pyrimidin-4-ylmethyl]-morpholine-3-carboxylic acid and Roferon A; 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid and Roferon A; 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid and Pegasys; or (2R,3S)-4-[(R)-6-(2-Chloro-3-fluoro-phenyl)-5-ethoxycarbonyl-2-thiazol-2-yl-3,6-dihydro-pyrimidin-4-ylmethyl]-2-methyl-morpholine-3-carboxylic acid and Pegasys; in a pharmaceutically acceptable carrier.

Another embodiment of present invention relates to use of pharmaceutical composition herein mentioned above as an antiviral medicament, in particular as the medicament for treatment or prophylaxis of hepatitis B virus infection.

Another embodiment of present invention relates to the use of an HBV capsid assembly inhibitor and an interferon for the manufacture of pharmaceutical composition herein mentioned above as an antiviral medicament, in particular the medicament for treatment or prophylaxis of hepatitis B virus infection.

EXAMPLES

The invention will be more fully understood by reference to the following examples. They should not, however, be construed as limiting the scope of the invention.

ABBREVIATIONS

3TC Lamivudine
CI Combination index
CL Confidence limit
CTG Cell Titer Glo
dHepaRG Differentiated HepaRG cells
DMSO Dimethyl sulfoxide
ETV Entecavir
FBS Fetal Bovine Serum
FIC Fractional inhibition concentration
FRG Fah-/-Rag2-/-Il2rg-/-
GE Genome equivalent
HBV Hepatitis B virus
IC50 Inhibitory Concentration 50%
IU/mL International unit per milliliter
µM Micromolar
min Minute
nM Nanomolar
PBS Phosphate buffered saline
PEG Polyethylene glycol
PHH Primary human hepatocyte
qPCR Real-time quantitative polymerase chain reaction
SD Standard deviation
sec Second
UDG Uracil DNA glycosylase
Materials and Methods
Virus and Cells
HepG2.2.15 Cells HepG2.2.15 cells were cultured in DMEM+Glutamax I medium (Gibco, #21885) supplemented with 10% FBS, 1% Pen/Strep (Gibco, #15140) and G-418 (250 µm/mL) and used for production of infectious HBV (genotype D). 90% confluent cells from three T175 flasks were trypsinized and transferred into one collagen coated hyperflask (550 mL). Once the cells were confluent, medium was changed to DMEM+Glutamax I medium with 1% DMSO and 2.5% FBS. Once the cells were slightly over confluent, medium was changed to DMEM/F12+Glutamax I medium (Gibco, #31331) supplemented with MEM non-essential aminoacids (6 mL, Gibco, #11140), P/S (6 mL), sodium pyruvate (6 mL), DMSO (9 mL) and FBS (10 mL) (all per 500 mL medium). Medium was changed every 3 days and supernatants were harvested for 2 weeks. Virus was concentrated from supernatants by PEG precipitation and the titer (genome equivalent (GE)/mL) was determined by qPCR. Briefly, supernatants were mixed with 40% PEG solution at a ratio of 4:1, incubated on a shaker at 4° C. overnight and then centrifuged using 50 mL falcon tubes at 4° C. for one hour at 3724 g (RCF). The supernatant was discarded and the centrifugation step was repeated with new supernatant reusing the tubes until all PEG-precipitated supernatant was processed. The pellets were re-suspended in William's E Medium (Gibco, #22551) at a concentration of $10^7$-$10^9$ genome equivalents (GE) per ml and frozen at $-80°$ C. DNA copy number calculation was based on a standard curve generated from HBV plasmid dilutions with known concentrations.

HepaRG Cells

HepaRG cells (Biopredic International, Saint-Gregoire, France) were cultured in working growth medium (500 mL Willams E Medium with 50 mL HepaRG Growth supplement from Biopredic, 5 mL Glutamax-I (Gibco, #35050) and 5 mL Pen/Strep) for 2 weeks. After 2 weeks, medium was changed to differentiation medium containing 1.8% DMSO (500 mL Willams E Medium with 50 mL HepaRG Growth supplement from Biopredic, 5 mL Pen/Strep, 5 mL Glutamax-I and 9 mL DMSO). Medium was changed twice a week up to 2 weeks. Once fully differentiated, cells were trypsinized and seeded into collagenated 96-well plates (50,000 cells/well in 100 μL) or 24-well plates (300,000 cells/well in 500 μL) in differentiation medium. Cells were cultured at least 5 days in the plates before they were infected with HBV.

PHH Cells

The HBV positive serum for infection in this study is obtained from FRG mice (WuxiAppTec, #34459) infected with an HBV patient serum (Genotype B, e negative), FRG mice were injected with $1\times10^9$ GE HBV via the tail vein. PHHs were isolated with two-step perfusion with collagenase using an extracorporeal perfusion apparatus at day 30 after inoculation, and PHHs were seeded in collagenated 24-well plates for ex vivo combination treatment.

Data Analysis and Calculation Model

Isobologram Model

The combination experimental results were analyzed using the model described by Craig et al. (Craig J, Duncan I, Whittaker L and Roberts N. (1990). Antiviral synergy between inhibitors of HIV proteinase and reverse transcriptase. *Antiviral Chem. Chemother.* 4:161-166). $EC_{50}$ values were obtained for compounds used alone and in combination with others. To relate these two values and describe the degree of synergy/additivity/antagonism between them, the Fractional Inhibitory Concentration (FIC) was first calculated and used to generate isobolograms. Briefly, the FIC is the ratio of the $EC_{50}$ of the drug in combination to the $EC_{50}$ of the drug on its own:

$$FIC=ratio[EC_{50combination}:EC_{50alone}]$$

The Combination Index (CI), obtained by adding the FICs of the two compounds, was then used to describe the effect between compounds used in the combinations. A CI<1 means synergism, a CI=1 means additivity and a CI>1 means antagonism.

CalcuSyn Model

Each experiment was performed in at least triplicate and performed independently 3 times. Mean percent inhibition of HBV replication based on DNA copy number was calculated from all experiments and analyzed using the Calcusyn software (CalcuSyn Version 2.11, Biosoft, Cambridge, UK) based on the Loewe additivity model described by Chou and Talalay (Chou T C (2006). Theoretical basis, experimental design, and computerized simulation of synergism and antagonism in drug combination studies. Pharmacol. Rev., 58:621-681). For the CalcuSyn evaluation, data from three diagonal lanes with a constant concentration ratio for the drug combinations of each lane from the checkerboard plate were used (marked in bold in Table 2). In a first step, this program converts the dose-effect curves for each drug or drug combination to median effect plots. A combination index (CI) for each experimental combination was then calculated by the following equation (for mutually nonexclusive interactions):

$$[(D)_1/(Dx)_1]+[(D)_2/(Dx)_2]+[(D)_1(D)_2/(Dx)_1(Dx)_2]$$

where $(Dx)_1$ and $(Dx)_2$ are the doses of drug 1 and drug 2 that have x effect when each drug is used alone, and $(D)_1$ and $(D)_2$ are the doses of drug 1 and drug 2 that have the same x effect when they are used in combination respectively. The software calculates the CIs at 50%, 75% and 90% antiviral effect of combinations. Combination effect assessment was based on overall CI values (average of CI values at 50%, 75% and 90% effect level) as follows: CI value <0.7 as synergy, 0.7 to 0.9 as slight to moderate synergy, 0.9 to 1.1 as additive, 1.1 to 1.5 as slight to moderate antagonism and >1.5 as antagonism (Chou TC (2006). Theoretical basis, experimental design, and computerized simulation of synergism and antagonism in drug combination studies. Pharmacol. Rev., 58:621-681). Drug combinations were analyzed at three different fixed drug ratios spanning and including the approximate ratio of their $EC_{50}s$.

MacSynergy Model

Each experiment was performed in at least triplicate. Mean percent inhibition of HBV replication based on DNA copy number was calculated from all experiments and analyzed using the MacSynergy TM II document (By Mark Neal Prichard, University of Michigan, USA).

This program allows the three-dimensional examination of two compounds with Bliss-Independence model. Confidence bounds are determined from replicate data. If the 95% confidence level does not overlap the theoretic additive surface, the interaction between the two drugs differs significantly from additive. The resulting surface would appear as a horizontal plane at 0% inhibition above calculated if the interactions are merely additives. Any peaks above the plane would be indicative of synergy. Similarly, any depression of the plane would indicate antagonism. The confidence intervals around the experimental dose-response surface are used to evaluate the data statistically and the volume of the peaks is calculated and used to quantitate the volume of synergy produced.

Example 1

Combination Study with Roferon in HepaRG Cells

For HBV infection of differentiated HepaRG cells, medium was removed and new differentiation medium (120 μL/well) containing 4% PEG-8000 and virus stock (20 to 30 GE/cell) was added. Cells were cultured at 37° C. for 16 to 20 hs before medium was removed, cells were washed 4 times with PBS and new differentiation medium (120 μL/well) was added. At day 4 post infection, medium was removed and 100 μL new differentiation medium was added to each well. 3-fold serial dilutions (5 µL compound to 10 µL DMSO) of Drug A and Drug B were prepared in 100% DMSO (HBV capsid assembly inhibitor) or in medium (Roferon) starting with 15 µL undiluted compound (400-fold concentration of highest test concentration). 5 µL of Drug A and Drug B dilutions were then added to 990 µL medium (containing 1.3% DMSO) in a 96-well plate in a checkerboard fashion according to the design shown in Table 2. 100 µL thereof were added to the dHepaRG cells with a final DMSO concentration of 1.8%. The concentration ranges tested were 100 nM to 1.23 nM for Drug A (Compound 1 or Compound 4), and 30 IU/mL to 0.04 IU/mL for Drug B (Roferon). Medium was replaced by new medium with compound at day 7 post infection and at day 11 post infection cell supernatants were harvested and directly used for HBV DNA extraction or stored at −20° C. Cell viability of the cells was determined using the cell viability assay described below.

Sequences for TaqMan Primers and Probes (IDT)

```
Forward core primer (F3_core):
                                        (SEQ ID: No. 1)
CTG TGC CTT GGG TGG CTT T Reverse primer (R3_core):
                                        (SEQ ID: No. 2)
AAG GAA AGA AGT CAG AAG GCA AAA Taqman probe (P3_core):
                                        (SEQ ID: No. 3)
56-FAM/AGC TCC AAA/ZEN/TTC TTT ATA AGG GTC
GAT GTC CAT G/3IABkFQ
```

Cell Viability Assay

Cell viability of the HBV infected and treated HepaRG cells was determined at day 11 post infection using the CellTiter-Glo® Luminescent Cell Viability Assay (Promega, Cat. No. G7572). 100 µL of CTG reagent were added to each well of the cells, incubated for 10 min and 80 µL of each well

TABLE 2

Plate layout for combinations with Roferon

|   | 1 | 2  | 3       | 4       | 5       | 6       | 7       | 8       | 9       | 10 | 11  | 12 |
|---|---|----|---------|---------|---------|---------|---------|---------|---------|----|-----|----|
| a | X | X  | X       | X       | X       | X       | X       | X       | X       | X  | X   | X  |
| b | X | A1 | A1 + B7 | A1 + B6 | A1 + B5 | A1 + B4 | A1 + B3 | A1 + B2 | A1 + B1 | VC | ETV | CC |
| d | X | A2 | A2 + B7 | A2 + B6 | A2 + B5 | A2 + B4 | A2 + B3 | A2 + B2 | A2 + B1 | VC | ETV | CC |
| d | X | A3 | A3 + B7 | A3 + B6 | A3 + B5 | A3 + B4 | A3 + B3 | A3 + B2 | A3 + B1 | VC | ETV | CC |
| e | X | A4 | A4 + B7 | A4 + B6 | A4 + B5 | A4 + B4 | A4 + B3 | A4 + B2 | A4 + B1 | VC | ETV | CC |
| f | X | A5 | A5 + B7 | A5 + B6 | A5 + B5 | A5 + B4 | A5 + B3 | A5 + B2 | A5 + B1 | VC | ETV | CC |
| g | X | VC | B7      | B6      | B5      | B4      | B3      | B2      | B1      | VC | ETV | CC |
| h | X | X  | X       | X       | X       | X       | X       | X       | X       | X  | X   | X  |

X: PBS
CC: cell control (uninfected)
VC: virus control
ETV: reference control (200 nM Entecavir)
A1-5: serial dilution of drug A
B1-7: serial dilution of drug B
A1 + B7: example of combination of drug A and B at different ratios DNA Extraction and qPCR HBV DNA from dHepaRG cell supernatants was extracted using the MagNA Pure 96 (Roche) robot. 100 µL of the supernatants were mixed in a processing cartridge with 200 µL MagNA Pure 96 external lysis buffer (Roche, Cat. No. 06374913001) and incubated for 10 minutes. DNA was then extracted using the "MagNA Pure 96 DNA and Viral Nucleic Acid Small Volume Kit" (Roche, Cat. No. 06543588001) and the "Viral NA Plasma SV external lysis 2.0" protocol. DNA elution volume was 50 µL.

Quantification of extracted HBV DNA was performed using a Taqman qPCR machine (ViiA7, life technologies). Each DNA sample was tested in duplicate in the PCR. 5 µL of DNA sample were added to 15 µL of PCR mastermix containing 10 µL TaqMan Gene Expression Master Mix (Applied Biosystems, Cat. No. 4369016), 0.5 µL PrimeTime XL qPCR Primer/Probe (IDT) and 4.5 µL distilled water in a 384-well plate and the PCR was performed using the following settings: UDG Incubation (2 min, 50° C.), Enzyme Activation (10 min, 95° C.) and PCR (40 cycles with 15 sec, 95° for denaturing and 1 min, 60° C. for annealing and extension). DNA copy numbers were calculated from $C_t$ values based on a HBV plasmid DNA standard curve by the ViiA7 software.

were transferred to a new white 96 well plate. Luminescence (0.2 sec) was measured using an Envision reader (PerkinElmer).

Combination Study

The interaction between Compound 1 and Roferon was analyzed using the CalcuSyn software. Study and calculation results are shown in Table 3, 4 and 5. The overall CI for three different concentration ratios was between 0.41 and 0.66, thus the combination of Compound 1 and Roferon is synergistic.

The interaction between Compound 1 and Roferon was also analyzed using the Isobologram model (FIG. 1). The FIC values for the combination of Compound 1 and Roferon were plotted one against the other for each of the experiments. The analysis showed that most of the CI values were <1. Therefore, the combination of Compound 1 and Roferon is synergistic.

The interaction between Compound 4 and Roferon was analyzed using the CalcuSyn software. Study and calculation results are shown in Table 3, 4 and 5. The overall CI for three different concentration ratios was between 0.69 and 0.77, thus the combination of Compound 4 and Roferon is moderate synergistic.

Figure 2:
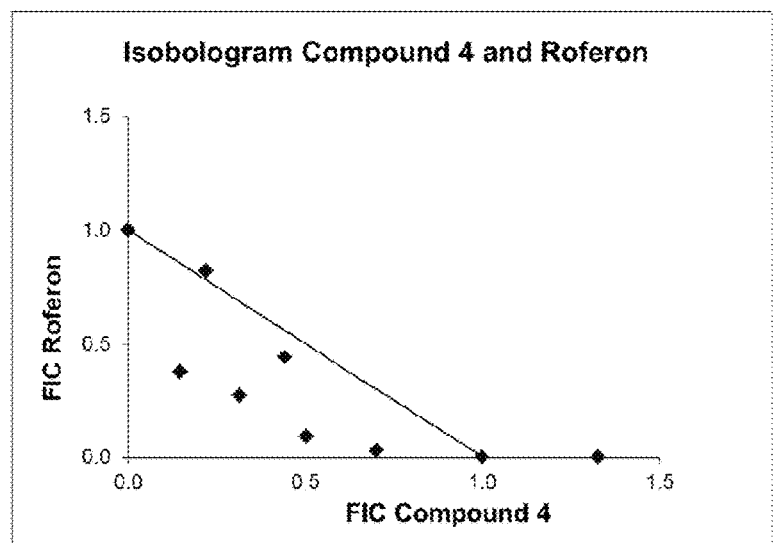
FIG. 2: Isobologram of FIC for the pair-wise checkerboard combination of Roferon and Compound 4 (at the 50% effect level). The diagonal lane connecting points (0, 1) and (1, 0) represents additivity (CI=1). Data points below this lane show synergism, data points above show antagonism. Shown are mean values from 3 independent experiments.

The interaction between Compound 4 and Roferon was also analyzed using the Isobologram model (FIG. 2). The FIC values for the combination of Compound 4 and Roferon were plotted one against the other for each of the experiments. The analysis showed that most of the CI values were <1. Therefore, the combination of Compound 4 and Roferon is synergistic.

None of the combinations had a significant effect on cell viability.

TABLE 3

Mean $EC_{50} \pm SD$ values for the individual compounds used in the combination studies

| Drug A | Drug B | $EC_{50} \pm SD$ (n) Drug A | $EC_{50} \pm SD$ (n) Drug B |
|---|---|---|---|
| 3TC | 3TC | 12.9 nM ± 6.4 (3) | 13.7 nM ± 1.0 (3) |
| Roferon | Compound 1 | 0.9 IU/mL ± 0.5 (3) | 21.2 nM ± 5.7 (3) |
| Roferon | Compound 4 | 1.8 IU/ml ± 1.7 (3) | 8.7 nM ± 2.0 (3) |

Results shown in Table 3 are mean $EC_{50} \pm SD$ values for the individual compounds in HBV infected HepaRG cells from n independent experiments.

TABLE 4

Cytotoxicity analysis for the individual compounds used in the combination studies

| Drug A | Drug B | % cell viability at max concentration ± SD (n) Drug A | % cell viability at max concentration ± SD (n) Drug B |
|---|---|---|---|
| 3TC | 3TC | 86.4 ± 2.6 (3) | 104.5 ± 2.6 (3) |
| Roferon | Compound 1 | 96.6 ± 9.3 (3) | 96.8 ± 4.2 (3) |
| Roferon | Compound 4 | 99.3 ± 2.7 (3) | 96.1 ± 14.5 (3) |

Results shown in Table 4 are mean % cell viability±SD at the maximum concentration of the individual compounds used to treat HBV infected HepaRG cells in n independent experiments. Cytotoxicity analysis was done to confirm that drugs did not show cytotoxic effect (also at high concentrations) which could interfere with antiviral activity.

HBV infected HepaRG cells were treated with different drug combinations and the effect on HBV DNA was evaluated using the CalcuSyn software, and the calculation results were shown in Table 5. Combination of 3TC and 3TC was used as additivity control in the assay.

Example 2

Combination Study with Pegasys in PHH Cells

PHH cells were isolated from HBV infected FRG mice and were seeded in collagenated 24-well plates for ex vivo combination treatment, and the next day HBV infected PHHs were treated with sequential combination of Compound 4 and Pegasys. The compound was first serially diluted in DMSO to make 100× of final concentration, and then further diluted with culture medium. Pegasys was serially diluted in culture medium to make 100× of final concentration, and then further diluted with culture medium. The final concentration of DMSO in the culture medium was 2%. From day 0 to day 6, HBV infected PHH cells were mono-treated with Compound 4 (B1: 3 μM, B2: 300 nM, B3: 30 nM, B4: 3 nM) for 6 days, 10 nM ETV (E) was used as control. The culture medium was refreshed with Compound 4 every 2 days, and the culture supernatant was collected every time. From day 6 on, PHH cells thereof were treated with Pegasys (A3: 0.03 IU/mL, A2: 0.3 IU/mL, A1: 3 IU/mL) and Compound 4 (B1: 3 μM, B2: 300 nM, B3: 30 nM, B4: 3 nM, 10 nM ETV as control) for another 24 days, then the culture medium was refreshed with above compounds every 2 days, and the culture supernatant was collected every time for analysis. Plate layout (in triplicate) was followed as Table 6.

TABLE 6

Plate layout for combinations with Pegasys in PHH cells

| | 1 | 2 | 3 | 4 | 5 | 6 |
|---|---|---|---|---|---|---|
| a | VC | B1 | B2 | B3 | B4 | ETV |
| b | A3 | A3 + B1 | A3 + B2 | A3 + B3 | A3 + B4 | ETV + A3 |

TABLE 5

CalcuSyn based combination indices for the pair-wise checkerboard combinations (HBV DNA)

| Drug combination | n[a] | Molar ratio | CI values at the following levels of HBV inhibition | | | Overall CI | Assessment[b] |
|---|---|---|---|---|---|---|---|
| | | | 50% | 75% | 90% | | |
| 3TC and 3TC | 3 | 1:0.3 | 1.12 ± 0.24 | 1.05 ± 0.16 | 1.02 ± 0.11 | 1.06 ± 0.16 | additivity |
| | | 1:1 | 0.98 ± 0.12 | 1.00 ± 0.14 | 1.06 ± 0.11 | 1.02 ± 0.11 | |
| | | 1:3 | 1.02 ± 0.22 | 1.03 ± 0.22 | 1.08 ± 0.21 | 1.04 ± 0.19 | |
| Compound 1 and Roferon | 3 | 0.03:1 | 0.48 ± 0.12 | 0.39 ± 0.12 | 0.37 ± 0.14 | 0.41 ± 0.12 | synergism |
| | | 0.1:1 | 0.63 ± 0.05 | 0.48 ± 0.08 | 0.44 ± 0.09 | 0.52 ± 0.11 | |
| | | 0.3:1 | 0.75 ± 0.21 | 0.61 ± 0.03 | 0.61 ± 0.15 | 0.66 ± 0.15 | |
| Compound 4 and Roferon | 3 | 0.03:1 | 0.72 ± 0.18 | 0.81 ± 0.22 | 0.76 ± 0.18 | 0.77 ± 0.17 | moderate synergism |
| | | 0.1:1 | 0.64 ± 0.14 | 0.65 ± 0.14 | 0.78 ± 0.20 | 0.69 ± 0.16 | |
| | | 0.3:1 | 0.72 + 0.16 | 0.64 ± 0.17 | 0.78 + 0.32 | 0.71 ± 0.21 | |

[a] Number of independent experiments
[b] Assessment was based on overall CI values as described above in section "Data Analysis and calculation model".

TABLE 6-continued

Plate layout for combinations with Pegasys in PHH cells

|   | 1  | 2       | 3       | 4       | 5       | 6        |
|---|----|---------|---------|---------|---------|----------|
| c | A2 | A2 + B1 | A2 + B2 | A2 + B3 | A2 + B4 | ETV + A2 |
| d | A1 | A1 + B1 | A1 + B2 | A1 + B3 | A1 + B4 | ETV + A1 |

VC: virus control
ETV: reference control (10 nM Entecavir)
A1-3: serial dilution of drug A
B1-4: serial dilution of drug B
A3 + B1: example of combination of drug A and B at different concentration
E + A1: example of combination of ETV and drug A as control DNA Extraction and qPCR The DNA in the serum was isolated with the QIAamp 96 DNA Blood Kit according to the manual and quantified by the real-time PCR (Fast Real-Time PCR System, ABI). 10 μ, of DNA sample were added to 15 μL of PCR mastermix containing 12.5 μ, mastermix, 1 μL HBV primers forward/ reverse, 0.5 μ, HBV specific probe in 96-well plate, a HBV plasmid DNA used for standards for DNA copies numbers calculation. qPCR was performed with 95° C. for 10 min, then cycling at 95° C. for 15 sec, 60° C. for 1 min for 40 cycles.

Sequences for TaqMan Primers and Probes:

```
Forward primer:
                                       (SEQ ID: No. 4)
5'-GTGTCTGCGGCGTTTTATCA-3'

Reverse primer:
                                       (SEQ ID: No. 5)
5'-GACAAACGGGCAACATACCTT-3'

Probe:
                                       (SEQ ID: No. 6)
FAM 5'-CCTCTKCATCCTGCTGCTATGCCTCATC-3' Tamra
```

Combination Study

Figure 3:
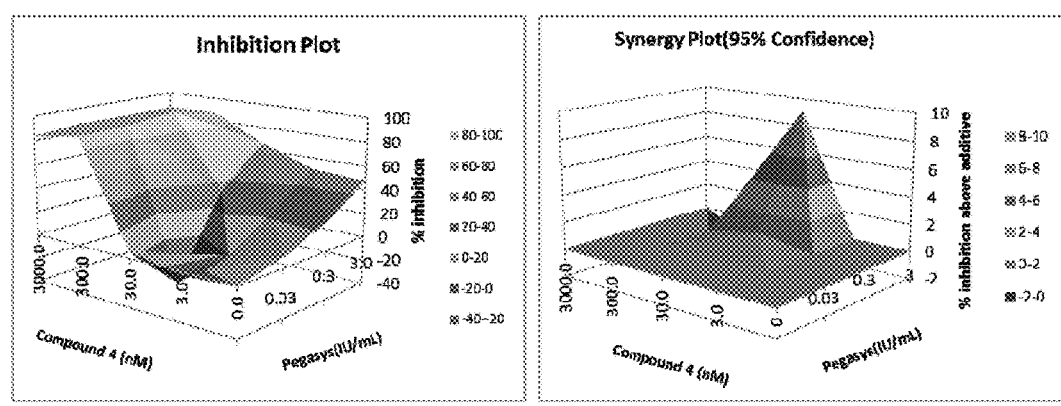
FIG. 3: Effects of Compound 4 and Pegasys combination in PHH cells. The left panel is the HBV DNA inhibition plot in the presence of Compound 4 and Pegasys with corresponding drug concentrations, and the inhibition percentage was calculated based on non-treated infection controls (VC as 0% inhibition) and positive drug controls (10 nM ETV as 100% inhibition); The additive drug interactions derived from 95% confidence interval data was shown in the right plot, which the calculated additive interactions were subtracted from the experimentally determined values based on average background, the peak is that with color indicate the level of synergy or antagonism (% inhibition above additive), and corresponding drug concentrations at which synergistic or antagonism interactions affecting antiviral activity.

The anti-HBV activity of combining Compound 4 and Pegasys on HBV DNA was examined, and the interaction between Compound 4 and Pegasys was analyzed using MacSynergy II (FIG. 3), the resulting surface showed peaks above the plane which indicative of synergy and the log volume is 9.79, thus the combination of Compound 4 and Pegasys is synergistic.

Example 3

Combination Study with Pegasys in HepaRG Cells dHepaRG cells were seeded in 24-well plate to recover for 7 days prior to HBV infection, and HBV virus (200 GE/cell) in differentiation medium (300 μL/well) containing 4% PEG-8000 was added to dHepaRG cells for 16 hours, then cells was washed with PBS for 3 times and new differentiation medium was added, culture medium was refreshed every 3 days. At day 13 post viral infection, HBV infected dHepaRG cells were treated with sequential combination of Compound 3 and Pegasys. The compound was first serially diluted in DMSO to make 100× of final concentration, and then further diluted with culture medium. Pegasys was serially diluted in culture medium to make 100× of final concentration, and then further diluted with culture medium. The final concentration of DMSO in the culture medium was 2%. From day 13, HBV infected HepaRG cells were mono-treated with Compound 3 (B1: 100 nM, B2: 20 nM, B3: 5 nM) for 5 days, 10 nM ETV (E) was used as control. The culture medium was refreshed including compound every 2.5 days, and the culture supernatant was collected every time. After 5 days mono-treatment, dHepaRG cells were treated with Pegasys (A1: 3 IU/mL, A2: 0.3 IU/mL, A3: 0.03 IU/mL) and Compound 3 (B1: 100 nM, B2: 20 nM, B3: 5 nM, ETV as control) for another 10 days, the culture medium was refreshed with above compounds every 2.5 days, and culture supernatant was collected every time for analysis. Plate layout (in triplicate) was followed as Table 7.

TABLE 7

Plate layout for combinations with Pegasys in HepaRG cells

|   | 1  | 2  | 3       | 4       | 5       | 6        |
|---|----|----|---------|---------|---------|----------|
| a | UC | VC | B1      | B2      | B3      | ETV      |
| b | VC | A1 | A1 + B1 | A1 + B2 | A1 + B3 | ETV + A1 |
| c | VC | A2 | A2 + B1 | A2 + B2 | A2 + B3 | ETV + A2 |
| d | VC | A3 | A3 + B1 | A3 + B2 | A3 + B3 | ETV + A3 |

UC: Uninfected control (pre-S1 peptide was used as entry inhibitor)
VC: virus control
ETV: reference control (10 nM Entecavir)
A1-3: serial dilution of drug A
B1-3: serial dilution of drug B
A1 + B1: example of combination of drug A and B at different concentration
E + A1: example of combination of ETV and drug A as control DNA Extraction and qPCR The DNA in the culture supernatant of indicated time was isolated with the MagNA pure 96 instrument according to the manual and quantified by the real-time PCR (Light Cycler 480 II, Roche). 5 μL of DNA sample were added to 15 μL of PCR mastermix containing 10 μL mastermix, 0.5 μL HBV primers forward/ reverse, 0.25 μL HBV specific probe and 3.75 μL ddH$_2$O in 384-well plate, a HBV plasmid DNA used for standards for DNA copies numbers calculation. PCR was performed with 95° C. for 10 min, then cycling at 95° C. for 15 sec, 60° C. for 1 min for 40 cycles.

Sequences for TaqMan Primers and Probes:

```
Forward primer:
                                       (SEQ ID: No. 7)
5'-AAGAAAAACCCCGCCTGTAA-3'

Reverse primer:
                                       (SEQ ID: No. 8)
5'-CCTGTTCTGACTACTGCCTCTCC-3'

Probe:
                                       (SEQ ID: No. 9)
5'-TAMRA + CCTGATGTGATGTTCTCCATGTTCAGC + BHQ2-3'
```

Figure 4:
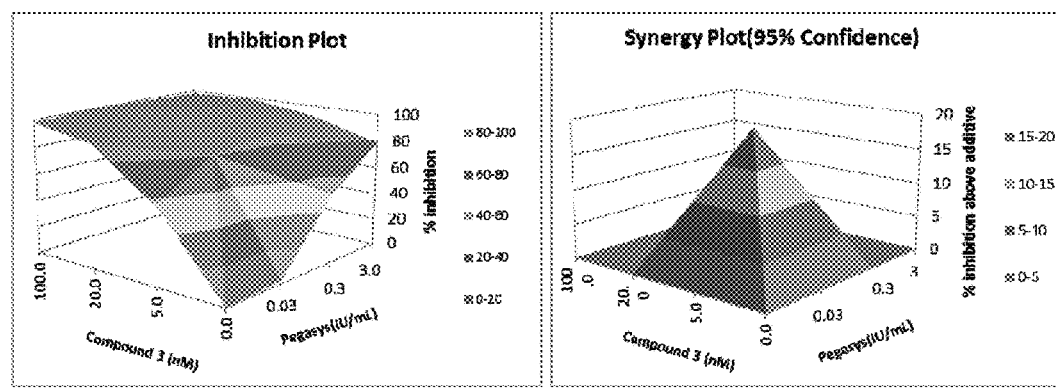
FIG. 4: Effects of Compound 3 and Pegasys combination in HepaRG cells. The left panel is the HBV DNA inhibition plot in the presence of Compound 3 and Pegasys with corresponding drug concentrations, and the inhibition percentage was calculated based on non-treated infection controls (VC as 0% inhibition) and positive drug controls (10 nM ETV as 100% inhibition); The additive drug interactions derived from 95% confidence interval data of compound 3 and Pegasys was shown in the right plot, which the calculated additive interactions were subtracted from the experimentally determined values based on average background, the peak is that with color indicate the level of synergy or antagonism (% inhibition above additive), and corresponding drug concentrations at which synergistic or antagonism interactions affecting antiviral activity.

Combination Study:

The anti-HBV activity of combining Compound 3 and Pegasys on HBV DNA was examined, and the interaction between Compound 3 and Pegasys was analyzed using MacSynergy II (FIG. 4), the resulting surface showed peaks above the plane which indicative of synergy and the log volume is 12.98, thus the combination of Compound 3 and Pegasys is synergistic.

The invention claimed is:

1. A pharmaceutical composition comprising an HBV capsid assembly inhibitor and an interferon, in a pharmaceutically acceptable carrier, wherein the HBV capsid assembly inhibitor is a compound of formula (III)

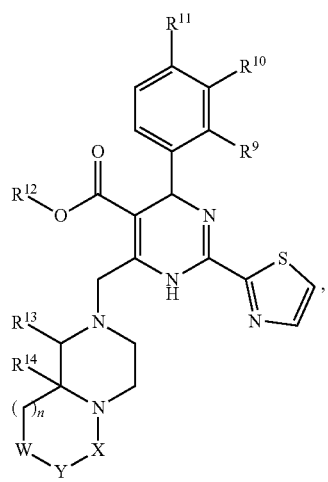

(III)

wherein:

$R^9$ is hydrogen, halogen or $C_{1-6}$alkyl;

$R^{10}$ is hydrogen or halogen;

$R^{11}$ is hydrogen or halogen;

$R^{12}$ is $C_{1-6}$alkyl;

$R^{13}$ is hydrogen, hydroxy$C_{1-6}$alkyl, aminocarbonyl, $C_{1-6}$alkoxycarbonyl or carboxy;

$R^{14}$ is hydrogen, $C_{1-6}$ alkoxycarbonyl or carboxy-$C_mH_{2m}$—;

X is carbonyl or sulfonyl;

Y is —CH$_2$—, —O— or —N(R$^{15}$)—, wherein R$^{15}$ is hydrogen, $C_{1-6}$alkyl, halo$C_{1-6}$alkyl, $C_{3-7}$cycloalkyl-$C_mH_{2m}$—, $C_{1-6}$alkoxycarbonyl-$C_mH_{2m}$—, —$C_tH_{2t}$—COOH, -halo$C_{1-6}$alkyl-COOH, —($C_{1-6}$alkoxy)$C_{1-6}$alkyl-COOH, —$C_{1-6}$alkyl-O—$C_{1-6}$alkyl-COOH, —$C_{3-7}$cycloalkyl-$C_mH_{2m}$-COOH, —$C_mH_{2m}$—$C_{3-7}$cycloalkyl-COOH, hydroxy-$C_tH_{2t}$—, carboxyspiro[3.3]heptyl, carboxyphenyl-$C_mH_{2m}$—, or carboxypyridinyl-$C_mH_{2m}$—;

W is —CH$_2$—, —C($C_{1-6}$alkyl)$_2$—, —O— or carbonyl;

n is 0 or 1;

m is 0, 1, 2, 3, 4, 5, 6, 7; and t is 1, 2, 3, 4, 5, 6, or 7;

or pharmaceutically acceptable salt, or enantiomer or diastereomer thereof.

2. The pharmaceutical composition according to claim 1, wherein HBV capsid assembly inhibitor is:

3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

3-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

4-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-3,3-dimethyl-butanoic acid;

(8S,8aR)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid; or (8R,8aS)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid;

or pharmaceutically acceptable salt, or enantiomer, or diastereomer thereof.

3. The pharmaceutical composition according to claim 1, wherein the interferon is a non-conjugated interferon alfa or a pegylated alfa-type interferon.

4. The pharmaceutical composition according to claim 1, wherein the composition is selected from:

3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid and Roferon A;

3-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid and Roferon A;

3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid and Roferon A;

4-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-3,3-dimethyl-butanoic acid and Roferon A;

(8S,8aR)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid and Roferon A;

(8R,8aS)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid and Roferon A;

3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid and Intron A;

3-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid and Intron A;

3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid and Intron A;

4-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-3,3-dimethyl-butanoic acid and Intron A;

(8S,8aR)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid and Intron A;

(8R, 8aS)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid and Intron A;

3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid and Pegasys;

3-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid and Pegasys;

3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid and Pegasys;

4-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-3,3-dimethyl-butanoic acid and Pegasys;

(8S,8aR)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid and Pegasys;

(8R,8aS)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid and Pegasys;

3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8 a-tetrahydro-1H-imidazo[1,5-a]pyrazin-2-yl]-2,2-dimethyl-propanoic acid and PegIntron;

3-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid and PegIntron;

3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid and PegIntron;

4-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-3,3-dimethyl-butanoic acid and PegIntron;

(8S,8aR)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid and PegIntron; and (8R,8aS)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid and PegIntron;

in a pharmaceutically acceptable carrier.

5. The pharmaceutical composition according to claim 1, wherein the composition is selected from the group consists of:

3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid and Roferon A; and 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid and Pegasys;

in a pharmaceutically acceptable carrier.

6. The pharmaceutical composition according to claim 1, wherein the interferon is Roferon A, Intron A, Pegasys or PegIntron.

7. The pharmaceutical composition according to claim 1, wherein the interferon is Roferon A or Pegasys.

8. A kit comprising a container that contains an HBV capsid assembly inhibitor and an interferon, wherein the HBV capsid assembly inhibitor is a compound of formula (III)

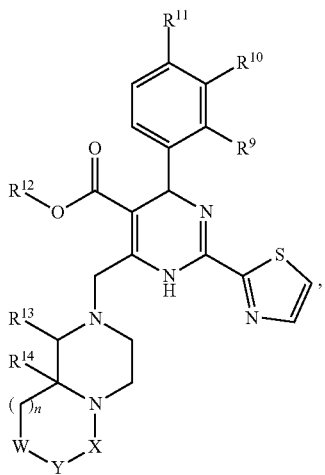

(III)

wherein:
$R^9$ is hydrogen, halogen or $C_{1-6}$alkyl;
$R^{10}$ is hydrogen or halogen;
$R^{11}$ is hydrogen or halogen;
$R^{12}$ is $C_{1-6}$alkyl;
$R^{13}$ is hydrogen, hydroxy$C_{1-6}$alkyl, aminocarbonyl, $C_{1-6}$alkoxycarbonyl or carboxy;
$R^{14}$ is hydrogen, $C_{1-6}$ alkoxycarbonyl or carboxy-$C_mH_{2m}$—;
X is carbonyl or sulfonyl;
Y is —$CH_2$—, —O— or —$N(R^{15})$—, wherein $R^{15}$ is hydrogen, $C_{1-6}$alkyl, halo$C_{1-6}$alkyl, $C_{3-7}$cycloalkyl-$C_mH_{2m}$—, $C_{1-6}$alkoxycarbonyl-$C_mH_{2m}$—, —$C_tH_{2t}$—COOH, -halo$C_{1-6}$alkyl-COOH, —($C_{1-6}$alkoxy)$C_{1-6}$alkyl-COOH, —$C_{1-6}$alkyl-O—$C_{1-6}$alkyl-COOH, —$C_{3-7}$cycloalkyl-$C_mH_{2m}$-COOH, —$C_mH_{2m}$—$C_{3-7}$cycloalkyl-COOH, hydroxy-$C_tH_{2t}$—, carboxyspiro[3.3]heptyl, carboxyphenyl-$C_mH_{2m}$—, or carboxypyridinyl-$C_mH_{2m}$—;
W is —$CH_2$—, —$C(C_{1-6}alkyl)_2$—, —O— or carbonyl;
n is 0 or 1;
m is 0, 1, 2, 3, 4, 5, 6, 7; and
t is 1, 2, 3, 4, 5, 6, or 7;
or pharmaceutically acceptable salt, or enantiomer or diastereomer thereof.

9. The kit according to claim 8, further comprising a sterile diluent.

10. The kit according to claim 8, further comprising a package insert comprising printed instructions directing the use of a combined treatment of the HBV capsid assembly inhibitor and the interferon as a method for treatment or prophylaxis of hepatitis B virus infection.

11. The kit according to claim 8, wherein the HBV capsid assembly inhibitor is:
3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;
3-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;
3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;
4-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-3,3-dimethyl-butanoic acid;
(8S,8aR)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid; or
(8R,8aS)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid;
or a pharmaceutically acceptable salt, or enantiomer, or diastereomer thereof.

12. The kit according to claim 8, wherein the interferon is a non-conjugated interferon alfa or a pegylated alfa-type interferon.

13. The kit according to claim 8, wherein the interferon is Roferon A, Intron A, Pegasys or PegIntron.

14. The kit according to claim 8, wherein the interferon is Roferon A or Pegasys.

15. The kit according to claim 8, wherein the HBV capsid assembly inhibitor and the interferon used in the container are:
3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid and Roferon A; or
3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid and Pegasys;
in a pharmaceutically acceptable carrier.

16. A method for treatment of hepatitis B virus infection, comprising:
administering to a subject an effective first amount of an HBV capsid assembly inhibitor, or a pharmaceutically acceptable salt, enantiomer or diastereomer thereof;
and a second amount of an interferon, wherein the HBV capsid assembly inhibitor is a compound of formula (III)

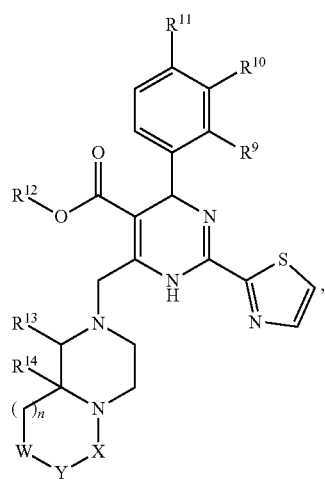

(III)

wherein:

$R^9$ is hydrogen, halogen or $C_{1-6}$alkyl;

$R^{10}$ is hydrogen or halogen;

$R^{11}$ is hydrogen or halogen;

$R^{12}$ is $C_{1-6}$alkyl;

$R^{13}$ is hydrogen, hydroxy$C_{1-6}$alkyl, aminocarbonyl, $C_{1-6}$alkoxycarbonyl or carboxy;

$R^{14}$ is hydrogen, $C_{1-6}$ alkoxycarbonyl or carboxy-$C_mH_{2m}$—;

X is carbonyl or sulfonyl;

Y is —$CH_2$—, —O— or —$N(R^{15})$—, wherein $R^{15}$ is hydrogen, $C_{1-6}$alkyl, halo$C_{1-6}$alkyl, $C_{3-7}$cycloalkyl-$C_mH_{2m}$—, $C_{1-6}$alkoxycarbonyl-$C_mH_{2m}$—, —$C_tH_{2t}$—COOH, -halo$C_{1-6}$alkyl-COOH, —($C_{1-6}$alkoxy)$C_{1-6}$alkyl-COOH, —$C_{1-6}$alkyl-O—$C_{1-6}$alkyl-COOH, —$C_{3-7}$cycloalkyl-$C_mH_{2m}$-COOH, —$C_mH_{2m}$—$C_{3-7}$cycloalkyl-COOH, hydroxy-$C_tH_{2t}$—, carboxyspiro[3.3]heptyl, carboxyphenyl-$C_mH_{2m}$—, or carboxypyridinyl-$C_mH_{2m}$—;

W is —$CH_2$—, —$C(C_{1-6}alkyl)_2$—, —O— or carbonyl;

n is 0 or 1;

m is 0, 1, 2, 3, 4, 5, 6, 7; and t is 1, 2, 3, 4, 5, 6, or 7.

17. The method according to claim 16, wherein the HBV capsid assembly inhibitor is:

3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

3-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid;

4-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-3,3-dimethyl-butanoic acid;

(8S,8aR)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid; or (8R,8aS)-2-tert-butyl-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazine-8-carboxylic acid;

or a pharmaceutically acceptable salt, or enantiomer, or diastereomer thereof.

18. The method according to claim 16, wherein the interferon is a non-conjugated interferon alfa or a pegylated alfa-type interferon.

19. The method according to claim 16, wherein the interferon is Roferon A, Intron A, Pegasys or PegIntron.

20. The method according to claim 16, wherein the interferon is Roferon A or Pegasys.

21. The method according to claim 16, wherein the HBV capsid assembly inhibitor and the interferon are:

3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid and Roferon A; or 3-[(8aS)-7-[[(4S)-5-ethoxycarbonyl-4-(3-fluoro-2-methyl-phenyl)-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid and Pegasys;

in a pharmaceutically acceptable carrier.

22. The method according to claim 16, wherein the HBV capsid assembly inhibitor and the interferon are co-administered in the same formulation or different formulations.

23. The method according to claim 16, wherein the HBV capsid assembly inhibitor and the interferon are administered to a subject by the same route or different routes.

24. The method according to claim 16, wherein the HBV capsid assembly inhibitor and the interferon are administered to a subject by parenteral or oral administration.

25. The method according to claim 16, wherein the HBV capsid assembly inhibitor and the interferon are administered simultaneously or sequentially.

* * * * *